US008217019B2

(12) United States Patent
Kano et al.

(10) Patent No.: US 8,217,019 B2
(45) Date of Patent: Jul. 10, 2012

(54) AIDS VIRUS VACCINES USING SENDAI VIRUS VECTOR

(75) Inventors: Munehide Kano, Hino (JP); Tetsuro Matano, Adachi-ku (JP); Atsushi Kato, Hamura (JP); Yoshiyuki Nagai, Toyama (JP); Mamoru Hasegawa, Tsukuba (JP)

(73) Assignees: DNAVEC Research Inc., Ibaraki (JP); Japan as Represented by the Director General of National Institute of Infectious Disease, Tokyo (JP)

( * ) Notice: Subject to any disclaimer, the term of this patent is extended or adjusted under 35 U.S.C. 154(b) by 0 days.

(21) Appl. No.: 12/701,303

(22) Filed: Feb. 5, 2010

(65) Prior Publication Data

US 2010/0266633 A1 Oct. 21, 2010

Related U.S. Application Data

(63) Continuation of application No. 09/823,699, filed on Mar. 30, 2001, now abandoned.

(60) Provisional application No. 60/193,127, filed on Mar. 30, 2000.

(51) Int. Cl.
*A61K 48/00* (2006.01)
*C12N 15/74* (2006.01)
*A01N 63/00* (2006.01)

(52) U.S. Cl. ...... 514/44; 435/320.1; 424/93.1; 424/93.2

(58) Field of Classification Search ........................ None
See application file for complete search history.

(56) References Cited

U.S. PATENT DOCUMENTS

| | | | |
|---|---|---|---|
| 5,766,945 A | 6/1998 | Miller | |
| 6,015,564 A | 1/2000 | Boutillon et al. | |
| 6,300,090 B1 | 10/2001 | Steinman et al. | |
| 6,645,760 B2 | 11/2003 | Nagai et al. | |
| 6,723,532 B2 | 4/2004 | Nagai et al. | |
| 6,746,860 B1 | 6/2004 | Tokusumi et al. | |
| 6,828,138 B1 | 12/2004 | Nagai et al. | |
| 7,101,685 B2 * | 9/2006 | Nagai et al. | 435/69.1 |
| 7,314,614 B1 | 1/2008 | Yonemitsu et al. | |
| 2002/0098576 A1 | 7/2002 | Nagai et al. | |
| 2002/0169306 A1 | 11/2002 | Kitazato et al. | |
| 2003/0166252 A1 | 9/2003 | Kitazato et al. | |
| 2003/0170210 A1 | 9/2003 | Masaki et al. | |
| 2003/0170266 A1 | 9/2003 | Kitazato et al. | |
| 2003/0170897 A1 | 9/2003 | Imai et al. | |
| 2003/0203489 A1 | 10/2003 | Yonemitsu et al. | |
| 2004/0005296 A1 | 1/2004 | Yonemitsu et al. | |
| 2004/0053877 A1 | 3/2004 | Fukumura et al. | |
| 2004/0101965 A1 | 5/2004 | Griesenbach et al. | |
| 2004/0121308 A1 | 6/2004 | Nagai et al. | |
| 2004/0265272 A1 | 12/2004 | Iwamoto et al. | |
| 2005/0266566 A1 | 12/2005 | Nagai et al. | |
| 2007/0269414 A1 | 11/2007 | Okano et al. | |
| 2008/0014183 A1 | 1/2008 | Okano et al. | |
| 2008/0031855 A1 | 2/2008 | Okano et al. | |
| 2009/0170798 A1 | 7/2009 | Hara et al. | |
| 2009/0246170 A1 | 10/2009 | Inoue et al. | |

FOREIGN PATENT DOCUMENTS

| | | |
|---|---|---|
| EP | 0863202 | 9/1998 |
| EP | 0864645 | 9/1998 |
| JP | 2000-253876 | 9/2000 |
| WO | WO 00/39302 | 7/2000 |
| WO | WO 00/70070 | 11/2000 |
| WO | WO 01/04272 | 1/2001 |

OTHER PUBLICATIONS

Hu et al. Virol 1990;179:321-9.*
Shiver et al. Vaccine 1997;15:884-7.*
Ramani et al. PNAS 1998;95:11886-90.*
Staars et al. AIDS Res Hum Retroviruses 1997;13:945-52.*
Adachi et al., "Production of Acquired Immunodeficiency Syndrome-Associated Retrovirus in Human and Nonhuman Cells Transfected with an Infectious Molecular Clone," *J. Virol.* 59:284-291 (1986).
Allen et al., "Effects of Cytotoxic T Lymphocytes (CTL) Directed Against a Single Simian Immunodeficiency Virus (SIV) Gag CTL Epitope on the Course of SIVmac239 Infection," *J. Virol.* 76:10507-10511 (2002).
Allen et al., "Tat-Vaccinated Macaques Do Not Control Simian Immunodeficiency Virus SIVmac239 Replication," *J. Virol.* 76:4108-4112 (2002).
Ayyavoo et al., "Construction of Attenuated HIV-1 Accessory Gene Immunization Cassettes," *Vaccine* 16:1872-1879 (1998).
Ayyavoo et al., "Immunogenicity of a Novel DNA Vaccine Cassette Expressing Multiple Human Immunodeficiency Virus (HIV-1) Accessory Genes," *AIDS* 14:1-9 (2000).
Brander et al., "Efficient Processing of the Immunodominant, HLA-A*0201-Restricted Human Immunodeficiency Virus Type 1 Cytotoxic T-Lymphocyte Epitope Despite Multiple Variations in the Epitope Flanking Sequences," *J. Virol.* 73:10191-10198 (1999).
Carruth et al., "An Algorithm for Evaluating Human Cytotoxic T Lymphocyte Responses to Candidate AIDS Vaccines," *AIDS Res. Hum. Retroviruses* 11:1021-1034 (1999).
Ciernik et al., "Induction of Cytotoxic T Lymphocytes and Antitumor Immunity with DNA Vaccines Expressing Single T Cell Epitopes[1]," *J. Immunol.* 156:2369-2375 (1996).

(Continued)

*Primary Examiner* — Q. Janice Li
(74) *Attorney, Agent, or Firm* — Clark & Elbing LLP

(57) ABSTRACT

The present invention provides a vaccine containing a Sendai virus vector encoding a virus protein of an immunodeficiency virus. By intranasally administering a Sendai virus encoding a virus protein of an immunodeficiency virus to a macaque monkey, the present inventors have succeeded in efficiently inducing protective immunity against an immunodeficiency virus. As a result of intranasal inoculation of vaccine, expression of an antigen protein mediated by Sendai virus vector was detected in intranasal mucous membrane and local lymph nodes and antigen-specific cellular immune response was induced at a significant level. No pathological symptom by vaccination was observed. After vaccination, exposure of simian immunodeficiency virus was performed and the effect was examined. As a result, the amount of virus in plasma significantly decreased, compared with that of the control animal. The present invention provides a promising vaccine as an AIDS vaccine.

17 Claims, 12 Drawing Sheets

OTHER PUBLICATIONS

Clontech, "BD RetroPack PT67 Cell Line," Online catalog and U.S. Patent No. 5,766,945 (2005).
Ensoli et al., "Control of Viral Replication and Disease Onset in Cynomolgus Monkeys by HIV-1 TAT Vaccine," *Journal of Biological Regulators and Homeostatic Agents* 14:579-590 (1998).
Flanagan et al., "A Recombinant Human Adenovirus Expressing the Simian Immunodeficiency Virus Gag Antigen Can Induce Long-Lived Immune Responses in Mice," *J. Gen. Virol.* 78:991-997 (1997).
Geffin et al., "Association of Antibody Reactivity to ELDKWA, a Glycoprotein 41 Neutralization Epitope, with Disease Progression in Children Perinatally Infected with HIV Type 1," *Aids Research and Human Retroviruses* 14:579-590 (1998).
Genome Database for Simian-Human Immunodeficiency Virus (SHIV), NCBI (2005).
Göttlinger et al., "Role of Capsid Precursor Processing and Myristoylation in Morphogenesis and Infectivity of Human Immunodeficiency Virus Type 1," *Proc. Natl. Acad. Sci. USA* 86:5781-5785 (1989).
Hanke et al., "Effective Induction of HIV-Specific CTL by Multi-Epitope using Gene Gun in a Combined Vaccination Regime," *Vaccine* 17:589-596 (1999).
Hasan et al., "Creation of an Infectious Recombinant Sendai Virus Expressing the Firefly Luciferase Gene from the 3' Proximal First Locus," *J. Gen. Virol.* 78:2813-2820 (1997).
Hirsch et al., "Patterns of Viral Replication Correlate with Outcome in Simian Immunodeficiency Virus (SIV)—Infected Macaques: Effect of Prior Immunization with a Trivalent SIV Vaccine in Modified Vaccinia Virus Ankara," *J. Virol.* 70:3741-3752 (1996).
HIV Envelop Protein, MeSH, NCBI (1990).
Hurwitz et al., "Intranasal Sendai Virus Vaccine Protects African Green Monkeys from Infection with Human Parainfluenza Virus-Type One," *Vaccine* 15:533-540 (1997).
IAVI Press Releases, Jan. 2008.
Ishioka et al., "Utilization of MHC Class I Transgenic Mice for Development of Minigene DNA Vaccines Encoding Multiple HLA-Restricted CTL Epitopes[1]," *J. Immunol.* 162:3915-3925 (1999).
Kano et al., "Elicitation of Protective Immunity Against Simian Immunodeficiency Virus Infection by a Recombinant Sendai Virus Expressing the Gag Protein," *AIDS* 14:1281-1282 (2000).
Kano et al., "Vaccine that Can Induce Gag-Specific Cellular Immunity: Analysis Using a Macaque Monkey Model," (Abstract 13pmH02) *The Japanese Society for Virology 48th Annual Meeting*, Abstracts: Vaccines (4), p. 278, Oct. 12, 2000.
Kano et al., "Induction of SIV-Specific Cellular Immune Responses by Using Recombinant Sendai Viral Vector," (Abstract) *7th Conference on Retroviruses and Opportunistic Infections* (2000).
Kano et al., "Induction of HIV-1-Specific Neutralizing Antibodies in Mice Vaccinated with a Recombinant Sendai Virus Vector," *Jpn. J. Infect. Dis.* 55:59-60 (2002).
Kast et al., "Failure or Success in the Restoration of Virus-Specific Cytotoxic T Lymphocyte Response Defects By Dendritic Cells," *J. Immunol.* 140:3186-3193 (1988).
Kato et al., "Induction of Gag-Specific T-Cell Responses by Therapeutic Immunization with a Gag-Expressing Sendai Virus Vector in Macaques Chronically Infected with Simian-Human Immunodeficiency Virus," *Vaccine* 24:3166-3173 (2005).
Kaur et al., "Identification of Multiple Simian Immunodeficiency Virus (SIV)-Specific CTL Epitopes in Sooty Mangabeys with Natural and Experimentally Acquired SIV Infection," *J. Immunol.* 164:934-943 (2000).
Kestler et al., "Induction of AIDS in Rhesus Monkeys by Molecularly Cloned Simian Immunodeficiency Virus," *Science* 248:1109-1112 (1990).
Leung et al., "The Kinetics of Specific Immune Responses in Rhesus Monkeys Inoculated with Live Recombinant BCG Expressing SIV Gag, Pol, Env, and Nef Proteins," *Virology* 268:94-103 (2000).
Matano et al., "Combined Use of Viral Vector and DNA as AIDS Vaccines: Analysis Using a Macaque Monkey Model," (Abstract 13pmH01) *The Japanese Society for Virology 48th Annual Meeting* Abstracts: Vaccines (4), p. 278, Oct. 12, 2000.
Matano et al., "No Significant Enhancement of Proetection by Tat-Expressing Sendai Viral Vector-Booster in a Macaque AIDS Model," *AIDS* 17:1392-1394 (2003).
Matano et al., "Cytotoxic T Lymphocyte-Based Control of Simian Immunodeficiency Replication in a Preclinical AIDS Vaccine Trial," *J. Exp. Med.* 199:1709-1718 (2004).
McCluskie et al., "Route and Method of Delivery of DNA Vaccine Influence Immune Responses in Mice and Non-Human Primates," *Mol. Med.* 5:287-300 (1999).
Moingeon et al., "Challenges and Issues in New Vaccine Development," *Trends Immunol.* 23:173-175 (2002).
Nakanishi et al., "Gene Transfer Vectors Based on Sendai Virus," *J. Control. Release* 54:61-68 (1998).
Nakano et al., "Immunization with Plasmid DNA Encoding Hepatitis C Virus Envelope E2 Antigenic Domains Induces Antibodies Whose Immune Reactivity is Linked to the Injection Mode," *J. Virol.* 71:7101-7109 (1997).
Ourmanov et al., "Comparative Efficacy of Recombinant Modified Vaccinia Virus Ankara Expressing Simian Immunodeficiency Virus (SIV) Gag-Pol and/or Env in Macaques Challenged with Pathogenic SIV," *J. Virol.* 74:2740-2751 (2000).
Persson et al., "Modifications of HIV-1 Retrovirus-Like Particles to Enhance Safety and Immunogenicity," *Biologicals* 26:255-265 (1998).
Robbins et al., "Viral Vectors for Gene Therapy," *Pharmacol. Ther.* 80:35-47 (1998).
Ruprecht et al., "1999: A Time to Re-evaluate AIDS Vaccine Strategies," *J. Hum. Virol.* 3:88-93 (2000).
Sakai et al., "Accommodation of Foreign Genes into the Sendai Virus Genome: Sizes of Inserted Genes and Viral Replication," *FEBS Lett.* 456:221-226 (1999).
Seth et al., "Recombinant Modified Vaccinia Virus Ankara-simian Immunodeficiency Virus *gag pol* Elicits Cytotoxic T Lymphocytes in Rhesus Monkeys Detected by a Major Histocompatibility Complex Class I/Peptide Tetramer," *Proc. Natl. Acad. Sci. USA* 95:10112-10116 (1998).
Subbramanian et al., "Magnitude and Diversity of Cytotoxic-T-Lymphocyte Responses Elicited by Multiepitope DNA Vaccination in Rhesus Monkeys," *J. Virol.* 77:10113-10118 (2003).
Takeda et al., "Protective Efficacy of an AIDS Vaccine, A Single DNA Priming Followed by a Single Booster with a Recombinant Replication-Defective Sendai Virus Vector, in a Macaques AIDS Model," *J. Virol.* 77:9710-9715 (2003).
Tomiyama et al., "Identification of Multiple HIV-1 CTL Epitopes Presented by HLA-B*5101 Molecules," *Hum. Immunol.* 60:177-186 (1999).
Torres et al., "Differential Dependence on Target Site Tissue for Gene Gun and Intramuscular DNA Immunizations," *J. Immunol.* 158:4529-4532 (1997).
Van Baalen et al., "Human immunodeficiency virus type 1 Rev- and Tat-Specific cytotoxic T lymphocyte frequencies inversely correlate with rapid progression to AIDS," *J. Gen. Virol.* 78:1913-1918 (1997).
Woodberry et al., "Immunogenicity of a Human Immunodeficiency Virus (HIV) Polytope Vaccine Containing Multiple HLA A2 HIV CD8[+] Cytotoxic T-Cell Epitopes," *J. Virol.* 73:5320-5325 (1999).
Yu et al., "Sendai Virus-based Expression of HIV-1 gp120: Reinforcement by the V(−) Version," *Genes Cells* 2:457-466 (1997).
Yu et al., "Regulatory and Accessory HIV-1 Proteins: Potential Targets for HIV-1 Vaccines?" *Curr. Med. Chem.* 12:741-747 (2005).
Reimann et al., "An env Gene Derived from a Primary Human Immunodeficiency Virus Type 1 Isolate Confers High In Vivo Replicative Capacity to a Chimeric Simian/Human Immunodeficiency Virus in Rhesus Monkeys," *J. Virol.* 70:3198-3206 (1996).
Barouch et al., "Reduction of Simian-Human Immunodeficiency Virus 89.6P Viremia in Rhesus Monkeys by Recombinant Modified Vaccinia Virus Ankara Vaccination," *J. Virol.* 75(11):5151-5158, 2001.

Cafaro et al., "Control of SHIV-89.6P-Infection of Cynomolgus Monkeys by HIV-1 Tat Protein Vaccine," *Nat. Med.* 5(6):643-650, 1999.

Ensoli et al., "Control of Viral Replication and Disease Onset in Cynomolgus Monkeys by HIV-1 TAT Vaccine," *J. Biol. Regul. Homeost. Agents* 14(1):22-26, 2000.

Gotoh et al., "Knockout of the Sendai Virus C Gene Eliminates the Viral Ability to Prevent the Interferon-α/β-Mediated Responses," *FEBS Lett.* 459(2):205-210, 1999.

Hu et al., "Role of Primary Constitutive Phosphorylation of Sendai Virus P and V Proteins in Viral Replication and Pathogenesis," *Virology* 263(1):195-208, 1999.

U.S. Appl. No. 11/922,278, filed Dec. 13, 2007, Yasuji Ueda et al., Title of Invention: Methods for Producing Antibodies.

Kent et al., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus," *J. Virol.* 72:10180-10188, 1998.

Matano et al., "Induction of Protective Immunity against Pathogenic Simian Immunodeficiency Virus by a Foreign Receptor-Dependent Replication of an Engineered Avirulent Virus," *Vaccine* 18:3310-3318, 2000.

Kahn, "An Interview with John Shiver: AIDS Vaccines, from Monkeys to People," *IAVI Report* 7(2):10-13, 2003.

Matano et al., "Rapid Appearance of Secondary Immune Responses and Protection from Acute CD4 Depletion after a Highly Pathogenic Immunodeficiency Virus Challenge in Macaques Vaccinated with a DNA Prime/Sendai Virus Vector Boost Regimen," *J. Virol.* 75:11891-11896, 2001.

\* cited by examiner

A

B

C

D

```
                        SEQUENCE LISTING

<160> NUMBER OF SEQ ID NOS: 18

<210> SEQ ID NO 1
<211> LENGTH: 10
<212> TYPE: DNA
<213> ORGANISM: Artificial Sequence
<220> FEATURE:
<223> OTHER INFORMATION: artificially synthesized sequence

<400> SEQUENCE: 1
ctttcaccct                                                              10

<210> SEQ ID NO 2
<211> LENGTH: 15
<212> TYPE: DNA
<213> ORGANISM: Artificial Sequence
<220> FEATURE:
<223> OTHER INFORMATION: artificially synthesized sequence

<400> SEQUENCE: 2
tttttcttac tacgg                                                        15

<210> SEQ ID NO 3
<211> LENGTH: 18
<212> TYPE: DNA
<213> ORGANISM: Artificial Sequence
<220> FEATURE:
<223> OTHER INFORMATION: artificially synthesized sequence

<400> SEQUENCE: 3
cggccgcaga tcttcacg                                                     18

<210> SEQ ID NO 4
<211> LENGTH: 18
<212> TYPE: DNA
<213> ORGANISM: Artificial Sequence
<220> FEATURE:
<223> OTHER INFORMATION: artificially synthesized sequence

<400> SEQUENCE: 4
atgcatgccg gcagatga                                                     18

<210> SEQ ID NO 5
<211> LENGTH: 18
<212> TYPE: DNA
<213> ORGANISM: Artificial Sequence
<220> FEATURE:
```

<223> OTHER INFORMATION: artificially synthesized sequence

<400> SEQUENCE: 5
gttgagtact gcaagagc                                                    18

<210> SEQ ID NO 6
<211> LENGTH: 42
<212> TYPE: DNA
<213> ORGANISM: Artificial Sequence
<220> FEATURE:
<223> OTHER INFORMATION: artificially synthesized sequence

<400> SEQUENCE: 6
tttgccggca tgcatgtttc ccaaggggag agttttgcaa cc                          42

<210> SEQ ID NO 7
<211> LENGTH: 18
<212> TYPE: DNA
<213> ORGANISM: Artificial Sequence
<220> FEATURE:
<223> OTHER INFORMATION: artificially synthesized sequence

<400> SEQUENCE: 7
atgcatgccg gcagatga                                                    18

<210> SEQ ID NO 8
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 8
tgggtgaatg agagaatcag c                                                21

<210> SEQ ID NO 9
<211> LENGTH: 32
<212> TYPE: DNA
<213> ORGANISM: Artificial Sequence
<220> FEATURE:
<223> OTHER INFORMATION: artificially synthesized sequence

<400> SEQUENCE: 9
aagcggccgc gagatgggcg tgagaaactc cg                                    32

<210> SEQ ID NO 10
<211> LENGTH: 63
<212> TYPE: DNA
<213> ORGANISM: Artificial Sequence
<220> FEATURE:
<223> OTHER INFORMATION: artificially synthesized sequence

<400> SEQUENCE: 10
ttgcggccgc gatgaacttt caccctaagt ttttcttact gtgactactg gtctcctcca      60
aag                                                                    63

<210> SEQ ID NO 11
<211> LENGTH: 20
<212> TYPE: DNA
<213> ORGANISM: Artificial Sequence
<220> FEATURE:
<223> OTHER INFORMATION: artificially synthesized sequence

<400> SEQUENCE: 11
agaaactccg tcttgtcagg                                                  20

```
<210> SEQ ID NO 12
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 12
tgataatctg catagccgc                                               19

<210> SEQ ID NO 13
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 13
gattagcaga aagcctgttg g                                            21

<210> SEQ ID NO 14
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 14
tgcaaccttc tgacagtgc                                               19

<210> SEQ ID NO 15
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 15
atgggatgtc ttgggaatc                                               19

<210> SEQ ID NO 16
<211> LENGTH: 21
<212> TYPE: DNA
<213> ORGANISM: Artificial Sequence
<220> FEATURE:
<223> OTHER INFORMATION: artificially synthesized sequence

<400> SEQUENCE: 16
ccaaatctgc agagtaccaa g                                            21

<210> SEQ ID NO 17
<211> LENGTH: 17
<212> TYPE: DNA
<213> ORGANISM: Artificial Sequence
<220> FEATURE:
<223> OTHER INFORMATION: artificially synthesized sequence

<400> SEQUENCE: 17
cagcttggag gaatgcg                                                 17

<210> SEQ ID NO 18
<211> LENGTH: 18
<212> TYPE: DNA
<213> ORGANISM: Artificial Sequence
```

-continued

```
<220> FEATURE:
<223> OTHER INFORMATION: artificially synthesized sequence

<400> SEQUENCE: 18
cttgttccaa gcctgtgc                                                   18
```

AIDS VIRUS VACCINES USING SENDAI VIRUS VECTOR

CROSS REFERENCE TO RELATED APPLICATIONS

This application is a continuation of U.S. patent application Ser. No. 09/823,699, filed Mar. 30, 2001, now abandoned which claims the benefit of the filing date of U.S. Provisional Patent Application Ser. No. 60/193,127, filed Mar. 30, 2000, the disclosures of which are incorporated by reference in their entirety.

FIELD OF THE INVENTION

The present invention relates to AIDS virus vaccines using a Sendai virus vector. The present invention also relates to a method for vaccination using a Sendai virus vector.

BACKGROUND OF THE INVENTION

Development of effective and safe vaccines against human immunodeficiency virus (HIV) infection is an urgent need to prevent the global dissemination of the virus. Some acquired immunodeficiency syndrome (AIDS) vaccine strategies have been evaluated in primate lentivirus infection models, but none of them has consistently induced sufficient resistance against the disease (Almond, N. M. and Heeney, J. L., 1998, AIDS 12 (Suppl. A): S133-140; Burton, D. R. and Moore, J. P., 1998, Nat. Med. 4: 495-498; Hulskotte, E. Q. et al., 1998, Vaccine 16: 904-915; Letvin, N. L., 1998, Science 280: 1875-1880).

Live viral vector-based vaccine is one of the promising prophylactic strategies because of its ability to induce efficient and durable antigen-expression (Cairns, J. S. and Sarver, N., 1998, AIDS Res. Hum. Retroviruses 14: 1501-1508; Hiresch, V. M. et al., 1996, J. Virol. 70: 3741-3752; Buge, S. L. et al., 1997, J. Virol. 71: 8531-8541). Poxvirus vectors have most often been used. There are a number of other options including adenoviruses. However, the attempts using these vectors have failed to elicit sufficient protective immunity against HIV. The efficiency to elicit protective immunity would be dependent on many factors such as the level and the duration of antigen-expression, the kinetics of the vector virus replication, and the tropism and the pathogenicity of the vector virus. Each viral vector currently available has both merit in some aspects and demerit in others. Precise evaluation and comparison of viral vectors would be required to find the optimal one.

One critical demerit of viral vector-based vaccine strategies is the induction of vigorous immune responses against the vector virus-derived antigens rather than the target antigens. This problem can be solved by using two or more different kinds of viral vectors for priming and boosting, respectively. DNA vaccine-based priming followed by viral vector-based boosting is also a favorable strategy (Hanke, T. et al. 1999, J. Virol. 73: 7524-7532; Robinson, H. L. et al., 1999, Nat. Med. 5: 526-534). Thus, development of a novel class of viral vectors is still waited for.

SUMMARY OF THE INVENTION

We previously established an efficient antigen-expression system using recombinant Sendai virus (SeV) (Kato, A. et al. 1996. Genes Cells 1:569-579). SeV, mouse parainfluenza virus type 1, is an enveloped virus with a nonsegmented negative sense RNA genome and belongs to the family Paramyxoviridae (Nagai, Y. 1999. Rev. Med. Virol. 9:83-99). The virus cause a fatal respiratory disease for mice but is believed to be non-pathogenic for nonhuman primates and humans (Nagai, Y. 1999. Rev. Med. Virol. 9:83-99; Hurwitz, J. L. et al., Vaccine 15: 533-540, 1997).

Because SeV replication occurs in the cytoplasm without a nuclear phase, even the lentivirus structural proteins such as Gag, Pol, and Env can be expected to be expressed efficiently via Rev-independent manner by using recombinant SeV vectors. More importantly, SeV vector can infect nondividing cells and there express foreign genes vigorously. For instance, the amount of human immunodeficiency virus type 1 (HIV-1) Env gp120 expressed by a recombinant SeV vector (V(−)SeV) reached as high as 6 µg/ml (corresponding to 6 µg per $10^6$ cells) in culture supernatant, the highest among those by vectors currently available in mammalian cell culture system (Yu, D. et al. 1997. Genes Cells 2:457-466). Here, to assess the feasibility of using a recombinant Sendai virus (SeV) vector as an AIDS vaccine, we have evaluated the ability of the system to elicit protective immunity against simian immunodeficiency virus (SIV) infection in macaques. We first created a mutant SeV, V(−)SeV, in which the V gene, which is one of accessory genes of SeV, was knocked out (Kato, A. et al. 1997. J. Virol. 71:7266-7272; Kato, A. et al. 1997. EMBO J. 16:578-587). This V(−)SeV was greatly attenuated in mice, but nevertheless its gene expression was rather augmented. From the aspects of both safety and efficiency, we have been using this V(−) version as the vector backbone. We then created a recombinant V(−)SeV expressing the Gag antigen of simian immunodeficiency virus strain mac 239 (SIVmac239) using V(−)SeV, here termed SeV/SIVgag, and its efficacy of anti-SIV immunity induction in macaque was assessed to examine the protective efficacy of its vaccination in a macaque AIDS model (Johnson, R. P. 1996. Curr. Opin. Immunol. 8:554-560; Almond, N. M., and Heeney, J. L. 1998. AIDS 12:133-140).

A recombinant SeV expressing SIV Gag, SeV/SIVgag, was recovered. SIV Gag-specific cellular immune responses induced by SeV/SIVgag-mediated Gag expression were examined in vitro. In cytotoxic T lymphocyte (CTL) assay SeV/SIVgag-infected cells worked as a Gag-specific CTL target. In peripheral blood lymphocyte culture, SeV/SIVgag-infected cells induced expansion of Gag-specific CTL population. In animal experiments using four cynomolgus macaques, two macaques were vaccinated with SeV/SIVgag by intranasal inoculation, one received a control SeV, and one was an unvaccinated control. Twenty-two weeks after the initial vaccination, these macaques were challenged intravenously with 100 TCID50 of SIVmac239. SIV challenge resulted in uniformly high plasma SIV loads in all the macaques during the acute phase. However, the subsequent viral loads in the SeV/SIVgag-vaccinated macaques were much lower than those (about $10^5$ copies/ml) in the controls and eventually fluctuate around the detectable level (100 copies/ml). It was showed that the vaccination using a SeV expressing structural proteins of SIV can remarkably decrease the viral amount in the chronic phase (set-point) after SIV challenge. The results suggest potential utility of SeV vector for a new AIDS vaccine as well as its availability for assessment of the cellular immune responses.

An objective of the present invention is to verify that efficient SIV Gag-expression was induced by using a recombinant SeV system and the feasibility of applying this system to AIDS vaccine development was indicated. Compared to poxvirus vectors widely used in AIDS vaccine studies, SeV vector is less cytotoxic and its antigen-expression levels are apparently higher in mammalian cells (Yu, D. et al., 1997, Genes Cells 2: 457-466). One of the characteristics of the SeV vector used in Examples is that the inserted gene is expressed more promptly and efficiently than any other SeV-specific genes derived from the vector because its accommodation is close to the 3'-terminus of the SeV genome (Nagai, Y., 1999, Rev. Med. Virol. 9: 83-99). This must be advantageous for efficient induction of the immune responses specific for the target antigen.

In the CTL assays, SeV/SIVgag-infected B-LCL worked well as the target for SIV Gag-specific CTL. In addition, coculture of normal peripheral blood mononuclear cells (PBMC) with SeV/SIVgag-infected PBMC led to IFN-γ induction and expansion of SIV Gag-specific CTL population. These results indicate that our SeV system is useful for assessing antigen-specific cellular immune responses. By using recombinant SeV vector, we can easily set up the coculture for CTL expansion without fixation or UV-irradiation, because SeV cannot infect cocultured cells without an exogenously added trypsin-like protease, that is required for processing of its inactive envelope protein precursor into an active form (Nagai, Y., 1993, Trends Microbiol. 1: 81-87).

Induction of the virus-specific cellular immune responses would be of value for protection against HIV-1 infection as has been indicated in recent reports (Geretti, A. M. et al., 1998, J. Gen. Virol. 79: 415-421; Matano, T. et al., 1998, J. Virol. 72: 164-169; Ogg, G. S. et al., 1998, Science 279: 2103-2106; Rowland-Jones, S. L. et al., 1998, J. Clin. Invest. 102: 1758-1765; Jin, X. et al., 1999, J. Exp. Med. 189: 991-998; Schmitz, J. E. et al., 1999, Science 283: 857-860). SeV/SIVgag-infected PBMC induced SIV Gag-specific CTL expansion. This suggests the ability of our system to induce antigen-specific cellular immune responses in vivo.

In the SIVmac239 challenge experiments, plasma SIV loads in the SeV/SIVgag-vaccinated cynomolgus macaques were comparable to those in the controls during the acute phase of infection. Thereafter, however, the SeV/SIVgag-vaccinated cynomolgus macaques showed significantly lower SIV loads. Particularly remarkable was that the viral loads remained at the lowest of or under the detectable level. Remarkable infection protection by using only a single antigen component (Gag) was also worthy to note. This reduction in the chronic phase (set-point) plasma viral loads might be due to high frequency of the activation of SIV Gag-specific T cell precursors. T cell precursor frequencies depend largely on the initial burst size in the natural course of virus infections. Extremely high performance of SeV in productivity of foreign antigens could be attributable to the presumable high T cell precursor frequency. However, re-administration of the same recombinant virus could be insufficient for boosting Gag-specific responses. It is thus feasible to prime with SeV/SIVgag and boost with a different viral vector, a DNA vaccine, and such (Amara, R. R. et al., Science, 8 Mar. 2001, 10.1126/science.1058915). While only Gag antigen was used for immunization in the Examples, expression of multiple antigens using recombinant SeV vectors may improve the protective efficacy.

Because SeV requires an envelope-processing protease for its replication, its replication tropism is restricted to particular tissues such as the epithelia of the airway (Nagai, Y., 1993, Trends Microbiol. 1: 81-87). No spread beyond the airway into other tissue is expected, suggesting a merit in terms of safety of SeV vector even in a replication competent form. Furthermore, induction of systemic mucosal immunity can be expected by intranasal administration of recombinant SeV vectors. This could be another advantage of SeV vector in prophylaxis against HIV-1 infection.

The present invention first disclosed the analysis of the primary SeV replication in primates. Its evaluation for efficiency, effectiveness, and safety in primates is essential before the clinical study, because efficiency of viral vector-based gene introduction depends on the host. The SeV replication in primates has not been characterized well, although there was a report examining the nasal swab samples from African green monkeys after intranasal inoculation with SeV (Hurwitz, J. L. et al. 1997. Vaccine 15:533-540). In our previous study, SeV/SIVgag expression was undetectable in macaque tissues including the nasal mucosa and the lung obtained at autopsy not less than one year after SeV/SIVgag inoculation (data not shown). In this study, we examined the antigen-expression on the primary phase and cellular immune responses in macaques vaccinated with a recombinant SeV vector. After macaques were inoculated intranasally with a recombinant SeV expressing SIV Gag (SeV/SIVgag), gag-expression and cellular immune responses in various tissues were examined. The SeV replication was controlled and the Gag-expression was restricted mainly in nasal mucosa and its local lymph nodes (LN). Robust gag-expression was observed in the nasal mucosa, and reduced but significant gag-expression in the local retropharyngeal and submandibular lymph nodes (LN). The expression peaked in not more than a week and lasted at least up to 13 days after the immunization. SeV/SIVgag was isolated from the nasal swabs certainly at day 4, less frequently at day 7, and not at all at day 13. On the other hand, there was no detectable antigen-expression in remote lymphatic tissues such as the thymus, the spleen, and the inguinal LN. Such tissue restriction and developmental sequence of SeV expression in monkeys is compatible with the SeV replication pattern in the natural host, mouse, which shows acute mucosal infection localized to airway epithelium but no generalized infection. However, the antigen was largely absent in the trachea and the lung, indicating that the spread of the virus was restricted in macaques compared with mouse. Further, analysis of cellular immune responses at day 7 showed quick appearance of SeV-specific CD8+ T cells. No monkeys displayed appreciable clinical manifestation after the immunization. Inoculation of SeV/SIVgag into nasal cavity of macaques led to efficient induction of Gag-specific CD8+ T cells. Gag-specific CD8+ T cells were detected at significant frequencies in the retropharyngeal LN as well as the peripheral blood mononuclear cells, indicating the potential of SeV to induce the antigen-specific cellular immune responses efficiently even in primates. Remarkably high frequencies of Gag-specific CD8+ T cells were detected systemically as well as locally after the immunization. These results further support the feasibility of using recombinant SeV vector as an AIDS vaccine.

As described above, efficient SeV/SIVgag expression dominant in the nasal mucosa and its local LN in SeV/SIVgag-vaccinated macaques was shown. While the detected gag RNA would be consisting of genomic RNA and mRNA, we confirmed the mRNA expression by using previously-established system to detect not SeV genomic N RNA but SeV N mRNA only (Kato, A. et al. 2001. *J. Virol. In press*). *The gag RNA level was higher than the SeV N mRNA level probably because the former contained the genomic RNA in addition to the mRNA. Another explanation is that the gag mRNA level is expected to be higher than the latter because the gag position is upstream to the N position in the genome (Nagai, Y. 1999. Rev. Med. Virol. 9:83-99).*

Intranasal inoculation comprises an advantage for induction of mucosal immune responses. The retropharyngeal LN and the submandibular LN receive the primary drainage of lymphocytes from the nasal cavity (Suen, J. Y., and Stern, S.

J. 1996. Cancer of the Neck. *In Cancer of the Head and Neck*, 3rd ed. E. N. Myers and J. Y. Suen, editors. W. B. Saunders Company, Philadelphia. 462-484). These LN are highly possible to be involved in the mucosal immune responses. Recently, the nasal-associated lymphoid tissue (NALT) has been indicated to play a role in mucosal immune responses in mice (Yanagita, M. et al., 1999, *J. Immunol.* 162:3559-3565). Cells prepared from Waldeyer's ring corresponding to NALT in mice were analyzed, and the SeV/SIVgag expression and the immune responses in the tissue can be verified. However, in the detection of the SeV/SIVgag expression in both the retropharyngeal LN and the submandibular LN, significant level of gag RNA was detected in both tissues. In these LN, no SeV replication is expected due to the absence of a protease essential for SeV protein processing (Nagai, Y. 1993. *Trends Microbiol.* 1:81-87) and the gag mRNA in the LN would be derived from the SeV/SIVgag-infected lymphocytes drained from the nasal cavity. The efficient antigen-expression in the local LN as well as the nasal mucosa by the intranasal SeV/SIVgag inoculation suggests SeV's potential for induction of mucosal immunity (Gallichan, W. S., and Rosenthal, K. L. 1996. *J. Exp. Med.* 184:1879-90).

Cellular immune responses have been shown to play an important role in controlling human and non-human primate lentiviruses such as HIV-1 and SIV (Ogg, G. S. et al. 1998. *Science* 279:2103-2106; Rowland-Jones, S. L. et al. 1998. *J. Clin. Invest.* 102:1758-1765; Brander, C., and Walker, B. D. 1999. *Curr. Opin. Immunol.* 11:451-459; Seder, R. A., and Hill, A. V. S. 2000. *Nature* 406:793-798). In macaque AIDS models, the importance of CD8+ T cells in controlling both primary and chronic infections has been shown by CD8+ T cell depletion using anti-CD8 antibody in vivo (Matano, T. et al. 1998. *J. Virol.* 72:164-169; Schmitz, J. E. et al. 1999. *Science* 283:857-860; Jin, X. et al. 1999. *J. Exp. Med.* 189:991-998). Thus, induction of virus-specific CD8+ T cell responses would be of high value for protection against HIV-1 infection. The antigen-specific T cell frequency detected by flow-cytometric analysis of intracellular cytokine induction is considered as an index of antigen-specific cellular immune responses, although it does not always correlate with antigen-specific cytotoxic activity (Lavini, A. et al. 1997. *J. Exp. Med.* 186:859-865; Butz, E. A., and Bevan, M. J. 1998. *Immunity* 8:167-175; Murali-Krishna, K. et al. 1998. *Immunity* 8:177-187; Donahoe, S. M. et al. 2000. *Virology* 272:347-356; Appay, V. et al. 2000. *J. Exp. Med.* 192:63-75). By using this technique, our study showed that SeV/SIVgag-infected cells could stimulate Gag-specific CD8+ T cells in vitro. Further, all the three macaques vaccinated with SeV/SIVgag detected high levels of Gag-specific CD8+ T cells in PBMC. Efficient induction of Gag-specific CD8+ T cells was also observed in the retropharyngeal LN. These results show that Gag-specific cellular immune responses were induced both systemically and locally by SeV/SIVgag vaccination.

No monkeys displayed appreciable clinical manifestation after the intranasal SeV/SIVgag vaccination. The SeV/SIVgag expression was localized largely in the nasal mucosa and its local LN, and its expression level reached the peak in not more than a week after the vaccination. Such expression pattern is compatible with the nature of SeV in the natural host, mouse. However, little expression of the antigen in the trachea and the lung indicates that the spread of the virus was restricted more strictly in macaques. Analysis of antigen-specific IFN-γ induction showed quick appearance of SeV-specific CD8+ T cells at week 1, suggesting the potential of cellular immune responses for controlling SeV replication. Thus, SeV/SIVgag replication was localized and controlled well in macaques. These results support the safety of our system in primates. In addition, safer system using a replication-incompetent SeV can be constructed.

Namely, the present invention first disclosed the primary antigen expression and cellular immune responses in macaques after an immunization mediated with a recombinant SeV. Our results showed not only efficient antigen expression but also efficient induction of antigen-specific cellular immune responses in all the intranasally-immunized macaques. The localized and well-controlled antigen-expression pattern supports the safety of the vector in primates. Taken together, the present study further indicates the SeV system as a promising tool for AIDS vaccine.

An objective of the present invention is to provide a vaccine containing a Sendai virus vector encoding a virus protein of an immunodeficiency virus. A vaccine of the present invention is extremely useful as an AIDS vaccine for prevention and treatment of AIDS. In addition, an objective of the present invention is to provide a method for vaccination by administering a vaccine of the present invention. Specifically, the present invention relates to:

(1) a vaccine comprising a Sendai virus vector encoding a virus protein of an immunodeficiency virus;

(2) the vaccine of (1), wherein the virus protein comprises Gag protein or a part of it;

(3) the vaccine of (1) or (2), wherein the Sendai virus vector is defective in V gene;

(4) a method for vaccination, the method comprising inoculating a vaccine comprising a Sendai virus vector encoding a virus protein of an immunodeficiency virus;

(5) the method of (4), wherein the vaccine is inoculated by intranasal administration;

(6) the method of (4) or (5), wherein the vaccine is inoculated at least once in multiple vaccine inoculation;

(7) the method of (6), wherein the method comprises the steps of (a) inoculating a DNA vaccine and then (b) inoculating the Sendai virus vector encoding a virus protein of an immunodeficiency virus; and (8) a method for inducing cellular immune response specific to a virus protein of an immunodeficiency virus, the method comprising the steps of (a) introducing a Sendai virus vector encoding a virus protein of an immunodeficiency virus into an antigen presenting cell and (b) contacting the antigen presenting cell with a T helper cell and a cytotoxic T cell.

The term "vaccine" used herein means a composition used for prevention or treatment of an infectious disease. A vaccine contains antibodies or can express antibodies, and thus, it can induce immune response against antigens. A vaccine of the present invention containing a Sendai virus vector can be used in a desired form for prevention or treatment of infection, dissemination, and epidemic of pathological microorganisms.

The term "vaccination" used herein means to actively generate immunity (humoral immunity, cellular immunity, or both) in a living body or in a culture system by inoculation of a vaccine. This can prevent infection, propagation, dissemination, and/or epidemic of pathogens. This can also repress onset and/or progress of symptom after infection of pathogens.

The term "antibody" used herein means a molecule that contains one or more epitopes and that can induce antigen-specific immune response by stimulating the immune system of a host. Immune response may be humoral immune response and/or cellular immune response. Although 3 to several amino acids can constitute an epitope, an epitope in a protein usually contains about 7 to about 15 amino acids, for example, 8, 9, 10, 12, or 14 amino acids. An antigen is called an immunogen. In the present invention, when a polynucleotide or a vector encoding an antigen protein is used for expressing an antigen, the polynucleotide or the vector is defined as an antigen. This can be used as a constituent of vaccines.

The term "immune response" or "immunological response" used herein means humoral immune response and/or cellular immune response against an antigen or a vaccine. Humoral immune response means immune response mediated by antibody molecules. Cellular immune response means immune response mediated by T lymphocytes and/or other leukocytes. Cellular immune response includes production of CTL, production or activation of helper T cells, or the like. Cellular immune response can be detected by examining cytokines or chemokines produced from activated T cells, such as CD8+ T cells, or other leukocytes. In addition, it can be determined by known lymphocyte proliferation assay, CTL assay, antigen-specific T cell assay, or the like.

The term "recombinant" used herein means a compound or a composition generated by mediating a recombinant polynucleotide. A recombinant polynucleotide is a polynucleotide in which nucleotide residues are bound not naturally. A recombinant protein can be obtained by expressing a recombinant polynucleotide. In addition, a "recombinant" virus vector is defined as that constructed by mediating a recombinant polynucleotide by genetic engineering or its amplified products.

The term "Paramyxovirus" used herein is defined as a virus of the Paramyxoviridae family. Paramyxoviruses include, but are not limited to, for example, Sendai virus, Newcastle disease virus, Mumps virus, Measles virus, Respiratory syncytial (RS) virus, rinderpest virus, distemper virus, simian parainfluenza virus (SV5), type I, II, and III human parainfluenza viruses, etc. Sendai viruses may be wild-type strains, mutant strains, laboratory-passaged strains, artificially constructed strains, or so on. Incomplete viruses such as the DI particle (J. Virol., 1994, 68, 8413-8417), synthesized oligonucleotides, and so on, may also be utilized as material for producing the vaccine of the present invention.

Genes encoding proteins of a Paramyxovirus include NP, P, M, F, HN, and L genes. Here, the "NP, P, M, F, HN, and L genes" represent those encoding the nucleocapsid protein, phosphoprotein, matrix protein, fusion protein, hemagglutinin-neuraminidase, and large protein, respectively. Genes of each virus of the subfamily Paramyxovirus are described generally as follows. In general, NP gene may also be indicated as "N gene".

| Paramyxovirus | NP | P/C/V | M | F | HN | — | L |
|---|---|---|---|---|---|---|---|
| Rublavirus | NP | P/V | M | F | HN | (SH) | L |
| Morbillivirus | NP | P/C/V | M | F | H | — | L |

For instance, the accession numbers in the nucleotide sequence database of each gene of the Sendai virus classified into the genus *Respirovirus* of Paramyxoviridae, are M29343, M30202, M30203, M30204, M51331, M55565, M69046, and X17218 for NP gene; M30202, M30203, M30204, M55565, M69046, X00583, X17007, and X17008 for P gene; D11446, K02742, M30202, M30203, M30204, M69046, U31956, X00584, X53056 for M gene; D00152, D11446, D17334, D17335, M30202, M30203, M30204, M69046, X00152, and X02131 for F gene; D26475, M12397, M30202, M30203, M30204, M69046, X00586, X02808, X56131 for HN gene; and D00053, M30202, M30203, M30204, M69040, X00587, and X58886 for L gene.

The term "gene" used herein is defined as a genetic substance, which includes nucleic acids such as RNA, DNA, etc. Genes may have naturally derived or artificially designed sequences. A Paramyxovirus vector used herein contains a foreign gene encoding the whole or a part of a virus protein of an immunodeficiency virus. The foreign gene may be a gene contained in a natural immunodeficiency virus or a fragment of the gene. The foreign gene also includes, for example, nucleic acids encoding natural virus proteins that are deleted, mutated, inactivated, or fused with another protein. In addition, herein, "DNA" includes a single stranded DNA or a double stranded DNA.

The term "immunodeficiency virus" used herein means a virus that causes immunodeficiency syndrome in humans or animals. Immunodeficiency syndrome means a pathological state in which normal immune mechanism is damaged by deficiency or malfunction of a part of or some of cell units constituting immune system. Pathogenicity of immunodeficiency virus is accompanied by disruption of immunocompetent cells mainly represented by CD4-positive T cells. Examples of immunodeficiency viruses include, in particular, human immunodeficiency virus (HIV), simian immunodeficiency virus (SIV), and such, which belongs to the subfamily lentivirus. HIV causes acquired immunodeficiency syndrome (AIDS) of humans. HIV includes type I (HIV-I) and type II (HIV-II). Herein, immunodeficiency viruses include all strains and subtypes of HIV-1 and HIV-2. In addition, herein, immunodeficiency viruses include all strains and subtypes of SIV. Many strains including SIVmac, SIVagm, SIVsm, and such are known as isolated strains of SIV. Besides, a feline immunodeficiency virus may be illustrated.

A virus protein means a protein contained in viruses. Virus proteins include structural proteins, regulatory proteins, and accessory proteins. Examples of main structural proteins of lentiviruses include Gag, Pol, and Env. Examples of main regulatory proteins of lentiviruses include Tat and Rev. Examples of main accessory proteins of lentiviruses include Vpu, Vpr, Vif, and Nef. In the present invention, an SeV vector encoding any of or a part of these proteins, or a combination of them is preferably used.

The term "naked DNA" used herein means a DNA not packed with proteins. Usually, a naked DNA is purified. The term "purified" means that the purity of a substance is higher than that of the substance in its natural state, and preferably, that the substance occupies a main ratio as a component of the sample in which the substance exists. DNAs can be purified by phenol and/or chloroform extraction, ethanol precipitation, PEG precipitation, PEG/NaCl precipitation, and such, and by appropriately combining known methods such as electrophoresis, cesium chloride ultracentrifugation, reverse phase column chromatography, gel filtration, HPLC, silica adsorption, etc. Naked DNAs include linearized and circular ones. For example, naked DNAs include plasmids, polymerase chain reaction (PCR) products, and purified or crude DNAs extracted from viruses, cells, and such. A naked DNA can be prepared as an artificial complex combined with buffers, salts, lipids, proteins, etc. For example, it may be prepared as a composition by combining it with a transfection agent such as a cationic lipid, etc. A DNA vaccine used herein means a vaccine containing a naked DNA as an ingredient.

The term "Sendai virus vector" used herein is defined as a vector (or carrier) that is derived from the Sendai virus and that is used for gene transfer to host cells. The Sendai virus may be ribonucleoprotein (RNP) or a virus particle having infectivity. Here, "infectivity" is defined as the ability of the recombinant Sendai virus vector to transfer, through its cell adhesion and membrane fusion abilities, a gene contained in the vector to cells to which the vector is adhered. The Sendai virus vector of the present invention carries, in an expressible manner, a foreign gene encoding an immunodeficiency virus protein, which can be an antigen. The Sendai virus vector may have the same replication ability as that of a wild-type vector or may be attenuated by gene mutation. In addition, a Sendai virus vector of the present invention may be a defective vector without the replication ability. Herein, "replication ability" is defined as the ability of virus vectors to replicate and produce infective virus particles in host cells infected with the virus vectors.

DETAILED DESCRIPTION OF THE INVENTION

Figure 1:
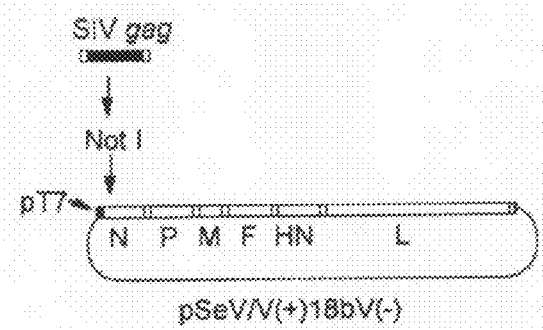
FIG. 1 shows SIV Gag-expression using SeV/SIVgag. (A) Structure of pSeV(+)18bV(−)/SIVgag, the constructed plasmid generating an antigenomic RNA of SeV/SIVgag. (B) Western blot analysis using a monoclonal mouse anti-p27 antibody. CV1 cells were lysed 24 hrs after mock infection (lane 1), SeV/control-infection (lane 2), or SeV/SIVgag-infection (lane 3). (C) Immnostaining using the anti-p27 antibody and an FITC-conjugated anti-mouse IgG antibody. CV1 cells were mock-transfected (a), or transfected with SHIV$_{MD14YE}$ DNA (Shibata, R. et al. 1997. *J. Infect. Dis.* 176:362-373) (b), or infected at m.o.i. of 0.05 with SeV/control (c) or SeV/SIVgag (d). (D) Replication kinetics of SeV/control and SeV/SIVgag in CV1 cells under multiple cycle growth condition in the presence of trypsin (7.5 μg/ml) (Sakai, Y. et al. 1999. *FEBS Lett.* 456: 221-226). At the initial infection, the cells were infected with SeV/control or SeV/SIVgag at m.o.i. of 0.05.
Figure 1:
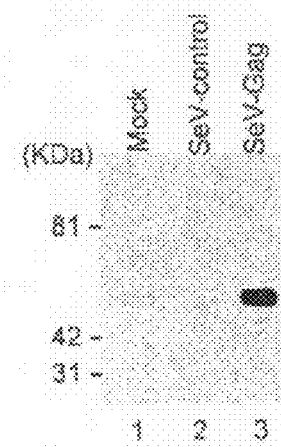
Figure 1:
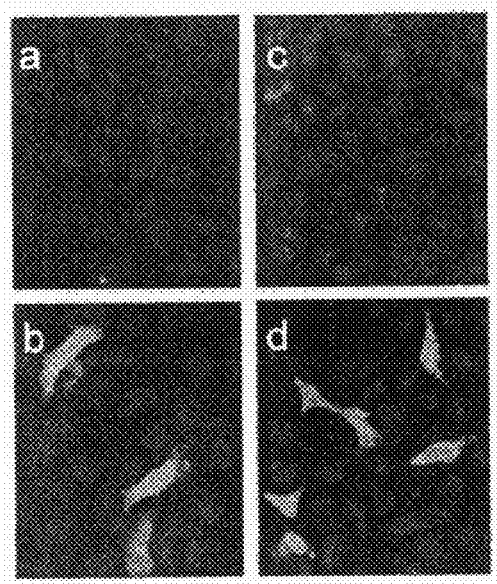
Figure 1:
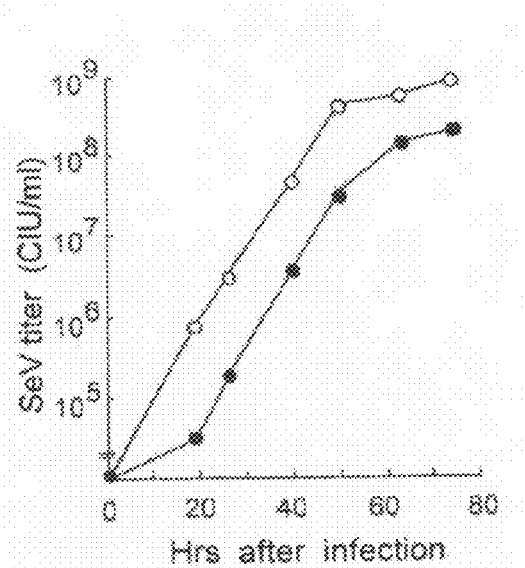

The present invention provides a vaccine containing a Sendai virus vector carrying, in an expressible manner, a foreign gene encoding an immunodeficiency virus protein or a part of the gene. There is no limitation on a Sendai virus-encoded virus protein of an immunodeficiency virus as long as the protein has immunogenicity. Virus proteins of an immunodeficiency virus include structural proteins, regulatory proteins, and accessory proteins of the virus. Examples of main structural proteins of lentiviruses, which included HIV-1, include Gag, Pol, and Env. Examples of main regulatory proteins of lentiviruses include Tat and Rev. Examples of main accessory proteins of lentiviruses include Vpu, Vpr, Vif, and Nef. These proteins, their partial peptides, and such are used for vaccine production. The vaccine can be produced by constructing a Sendai virus vector expressing the above-mentioned proteins or parts of them. These proteins may be used alone or by combining two or more of them. In the present invention, it is preferable, in particular, to use an SeV expressing structural proteins of an immunodeficiency virus. Specifically, an SeV expressing full-length Gag protein, Gag-Pol fusion protein, a fragment of them, or the like can be used.

The present inventors showed that gene expression from a recombinant SeV vector that had been intranasally inoculated to a macaque monkey reached a peak within a week after the inoculation and persisted until at least day 13. In addition, repetitive administration enables the expression to persist. These features are advantageous in obtaining a fast and sustained therapeutic effect in vaccination using recombinant SeV vectors.

SeV vectors can be preferably utilized in clinical application to humans in terms of safety as well. First, in the case of many vectors, it is a major obstacle in high efficient gene transfer that transfected DNA must be transported into the nucleus for the expression of a foreign gene. In the case of Sendai virus and such, however, expression of a foreign gene is driven by both cellular tubulin. and its RNA polymerase (L protein) in the cytoplasm. This suggests that the SeV does not interact with the genome of host cells, which avoids safety problems such as tumorigenesis. Second, the SeV is known to be pathogenic in rodents causing pneumonia, but not in humans, which is supported by studies showing that the intranasal administration of the wild-type SeV does not do harm in nonhuman primates (Hurwitz J. L. et al., Vaccine, 1997, 15, 533-540). These features suggest that SeV vector is highly safe when applied to humans, and further, support the notion that Sendai virus can be one of the promising alternatives for vectors that is aimed at expression of antigen proteins for vaccination. In fact, significant expression of an antigen was detected in a primate, macaque monkey, inoculated with SeV in the present invention. In addition, inoculation of an SeV virus itself did not show any definite pathological symptom and significant decrease in the number of peripheral CD4 or CD8 cells was not observed.

The vaccine of the present invention may be preferably utilized in vaccination specifically targeting an AIDS virus. In other words, inoculation of a vaccine of the present invention enables inducing immunity against an immune deficiency virus and preventing infection and/or propagation of the virus. A vaccine of the present invention is preferably used for prevention before infection of an immune deficiency virus and for treatment after the infection.

The SeV vector of the present invention used for vaccination is not limited to any special kind. For instance, vectors that have the replication ability and that are capable of autonomous propagation may be preferably utilized. In general, the genome of the wild-type SeV contains a short 3' leader region followed by six genes encoding N (nucleocapsid), P (phospho), M (matrix), F (fusion), HN (hemagglutinin-neuraminidase), and L (large) proteins, and has a short 5' trailer region on the other terminus. The vector that is able to replicate autonomously can be obtained by designing a genome having a similar structure to that described above. In addition, a vector for expressing a foreign gene can be obtained by inserting the foreign gene to the genome of the above vector. The SeV vector may have an altered alignment of virus genes, compared with wild-type virus.

The SeV vector of the invention may have deletion(s) of some of the genes that are contained in the wild-type SeV. For instance, to reconstitute the SeV vector and to express the genes, proteins encoded by NP, P/C, and L genes are thought to be required, and therefore, the genes must be a component of the SeV vector. However, SeV vector can be reconstituted by providing M, F, and HN proteins in trans and gene expression from the vector is possible. An expression vector carrying genes encoding these proteins may be co-transfected into host cells with another expression vector encoding the vector genome to reconstitute SeV vector. Alternatively, an expression vector encoding the virus genome is transfected into host cells carrying genes encoding the proteins, and thus a virus vector can be reconstituted by using the proteins provided by the host cell. The amino acid sequence of these proteins may not be identical to those derived from the original virus as long as it has an equivalent or higher activity in nucleic acid transfer, and may be mutated or replaced with that of a homologous gene of another virus.

When the SeV vector is prepared as RNP, proteins encoded by M, F, and HN genes, which are thought to be essential for cell-to-cell propagation of an SeV vector, are not required. If genes M, F, and HN are components of the genome contained in RNP, products of these genes are produced when introduced into host cells, and virus particles having infectivity are generated. RNP vectors that produce an infective virus include a virus genome RNA encoding N, P, M, F, HN, and L genes and RNP containing N, P, and L proteins. When such RNP is introduced into cells, virus genome is expressed and replicated through functions of the proteins, and thus infective virus vectors are amplified.

RNP can be introduced into cells as a complex formed with lipofectamine, polycationic liposome, and the like. Specifically, a variety of transfection reagents can be used, for instance, DOTMA (Boehringer), Superfect (QIAGEN #301305), DOTAP, DOPE, DOSPER (Boehringer #1811169). Chloroquine may be added to prevent degradation in the endosome (Calos M. P. , Proc. Natl. Acad. Sci. USA, 1983, 80, 3015). In the case of replicative viruses, the produced viruses can be amplified or passaged by re-infecting into cultured cells, chicken eggs, or animals (e.g. mammalian such as mice).

Contrastingly, the SeV vector lacking the M, F, and/or HN genes is also preferable as those used for vaccine of the present invention. These vectors can be reconstituted by providing deleted gene products exogenously. Such vectors can still adhere to host cells and induce cell fusion as the wild type. However, daughter virus particles do not have the same infectivity as the original ones because the vector genome introduced into cells lacks one of the above genes. Therefore, these vectors can be useful as safe virus vectors that are capable of only a single gene transfer. For instance, genes deleted from the genome may be F and/or HN genes. Virus vectors can be reconstituted by co-transfection of an expression plasmid encoding the genome of a recombinant Paramyxovirus lacking the F gene, an expression vector for the F protein, and that for NP, P/C, and L proteins into host cells (WO00/70055 and WO00/70070). Alternatively, host cells in which the F gene is integrated into the chromosome may be used. The amino acid sequence of these proteins provided exogenously may not be identical to those of the wild type and may be mutated or replaced by a homologous protein of another virus as long as they provide equivalent or higher gene transfer activity.

The envelope protein of the SeV vector of the invention may contain another protein than the envelope protein of the original vector genome. There is no limitation on such proteins. These may include envelope proteins of other viruses such as the G protein of the vesicular stomatitis virus (VSV-G). Thus, the SeV vector constituting the vaccine of the invention includes a pseudo type virus vector that has an envelope protein derived from a virus different from the original virus.

Also, the SeV vector used for the vaccine of the invention may have on the surface of its envelope a protein targeted at particular cells such as adhesion molecules, ligands, and receptors, or a chimeric protein having these proteins in its extracellular domain and a polypeptide derived from the virus envelope protein in its intracellular domain. It enables the production of a vector targeting a particular tissue. These proteins may be encoded by the virus genome itself, or supplied at the time of virus reconstitution through expression of genes other than virus genome (for example, another expression vector or host cell chromosome).

The virus genes contained in the SeV vector used for the vaccine of the invention may be altered to reduce antigenicity against SeV proteins or enhance RNA transcription efficiency or replication efficiency. Specifically, it is possible to alter at least one of the NP, P/C, and L genes, which are genes of replication factors, to enhance transcription or replication. It is also possible to alter the HN protein, a structural protein having hemagglutinin activity and neuraminidase activity, to enhance the virus stability in blood by weakening the former activity and to regulate infectivity by altering the latter activity. It is also possible to alter the F protein, which is implicated in membrane fusion, to regulate the fusion ability of membrane-fused liposomes. Furthermore, it is possible to generate an SeV that is engineered to have weak antigenicity against these proteins through analyzing the antigen presenting epitopes and such of possible antigenic molecules on the cell surface such as the F protein and HN protein.

In addition, SeV whose accessory gene is deleted can be used for the vaccine of the present invention. For example, when V gene, one of the accessory genes of SeV, is knocked out, pathogenicity of SeV to mice markedly decreases without damages to the expression and replication of genes in cultured cells (Kato, A. et al. 1997. J. Virol. 71: 7266-7272; Kato, A. et al. 1997. EMBO J. 16: 578-587; Curran, J. et al., WO01/04272, EP1067179). Such attenuated vectors are particularly preferable as vectors constituting the vaccine of the present invention.

The virus vector used for the vaccine of the present invention encodes a virus protein of an immunodeficiency virus or a part of the protein in its genomic RNA. Such recombinant SeV vector expressing a foreign gene can be obtained by inserting the foreign gene into the above-mentioned SeV vector genome. Examples of the foreign gene include a gene fragment encoding a virus protein of an immunodeficiency virus or a part of the protein. Examples of the gene fragment include a naturally occurring gene fragment encoding an immunodeficiency virus protein and, in addition, a gene encoding a natural protein modified by deletion, substitution, insertion, or the like as long as it encodes a protein having antigenicity at least partially equivalent to that of a natural protein.

Virus proteins of immunodeficiency viruses including HIV include structural proteins, regulatory proteins, and accessory proteins. Examples of main structural proteins of lentiviruses include Gag, Pol, and Env. Examples of main regulatory proteins of lentiviruses include Tat and Rev. Examples of main accessory proteins of lentiviruses include Vpu, Vpr, Vif, and Nef. In the present invention, an SeV vector encoding these proteins, a part of them, or a combination of them is preferably used.

For example, in HIV-1, Gag is expressed as a 55-kD precursor protein called p55 and cleaved by pol gene-encoded protease to generate MA (matrix, p17), CA (capsid, p24), NC (nucleocapsid, p9), and p6 (Gottlinger, H. G. et al., Proc. Natl. Acad. Sci. USA 1989,86: 5781-5785). pol gene encodes virus protease (Pro), integrase (IN), RNaseH, and reverse transcriptase (RT), and is first expressed as Gag-Pol fusion protein (Jacks, T. et al., Nature 1988, 331: 280-283). Gag-Pol precursor (p160) is generated by frameshift, which occurs at a frequency of about 5% when ribosome translates. Pol polypeptide is cleaved from Gag by virus-encoding protease and further cleaved to protease (p10), RT (p50), RNaseH (p15), and integrase (p31). In addition, incompletely cleaved fragments, such as polypeptide (p65), in which RT protein and RNaseH is linked, also exist. Env (160 kD, gp160) is cleaved to gp41 and gp120 by cellular protease. gp120 interacts with CD4, which is a receptor existing at the surface of target cells, CCR5, which is a co-receptor, and such in virus infection (Berger, E. A. et al., Annu. Rev. Immunol. 1999, 17: 657-700). In addition, gp120 has hypervariable regions called V1-V5. These regions are comparatively greatly different depending on isolated strains and, among them, the region called V3 loop affects virus tropism (Hwang, S. S. et al., Science 1991, 253: 71-74). V3 loop is a main target of a neutralizing antibody for preventing HIV infection (Goudsmit, J, et al., Proc. Natl. Acad. Sci. USA 1988, 85: 4478-4482).

Tat, a transcription transactivator essential for virus replication, is expressed as multiple peptides having different length from one another (Ruben, S. et al., J. Virol. 1989, 63: 1-8). Rev is an about 13-kD sequence-specific RNA binding protein (Zapp, M. L. and Green, M. R., Nature 1989, 342: 714-716) and regulates the phase of virus gene expression by binding to Rev response element (RRE). Besides these genes, HIV-1 has four genes, nef, vif, vpr, and vpu, encoding accessory proteins. HIV-2 has vpx instead of vpu.

SeV vector is constructed so as to express the full length of any of these virus proteins, including processed and unprocessed proteins, a part of them, or a combination of them. There is no limitation on the length, position, and such of the part as long as the part has an activity of antigen. For example, a partial peptide containing one or more epitopes is included. Such partial peptide usually contains at least 3 to several contiguous amino acids in the amino acid sequence of a virus protein. Preferably, the peptide contains about 7 to about 15 contiguous amino acids, for example, 8, 9, 10, 12, or 14 amino acids in the amino acid sequence of a virus protein.

At least one type of virus protein of an immunodeficiency virus is used for the vaccine. The present invention enables inducing efficient immune response even if only Gag antigen is expressed. In addition, by using multiple types of proteins as antigens, more efficient immunity can be acquired.

In addition, virus proteins derived from one type of virus among immunodeficiency viruses is used for the vaccine, but by using, as antigens, virus proteins derived from multiple types of viruses, immunity against immunodeficiency viruses of more wide-range strains and subtypes. In the case that multiple types of immunodeficiency viruses are used as antigens, there is no limitation on the combination of them. For example, vaccine can be produced by using a gene derived from various kinds of isolated strains of HIV-1, HIV-2, or SIV. After SeV is constructed by integrating multiple immunodeficiency virus genes into different SeV vector genomes, vaccine can be produced by combining or mixing the SeV. Alternatively, multiple genes can be expressed by integrating them into the same SeV vector gemone.

For example, HIV-1 includes all major (M) subtypes, including A to J, N, and outlier (O) (Hu, D. J. et al., JAMA 1996, 275: 210-216; Zhu, T. et al., Nature 1998, 5, 391(6667): 594-7; Simon, F. et al., Nat. Med. 1998, 4(9): 1032-7).

Examples of isolated strains of SIV include SIVagm, SIVcpz, SIVmac, SIVmnd, SIVsnm, SIVsyk, etc.

As an immunodeficiency virus from which virus proteins used for the vaccine of the present invention are derived, in particular, an immunodeficiency virus whose host is a primate is preferable. Examples of such virus include HIV-1, HIV-2, and SIV.

It is highly likely that immunity against a virus of one strain or subtype can be acquired to some extent by vaccination in which a virus protein of one type of immunodeficiency virus belonging to another strain is used as an antigen, if the amino acid sequences of the virus proteins of the two viruses are highly homologous.

For instance, to construct SeV expressing a virus protein of an immunodeficiency virus, for example, a gene encoding a virus protein of a target immunodeficiency virus may be inserted into the DNA encoding the SeV genome (the SeV vector DNA). In the case of inserting a foreign gene into SeV vector DNA, a sequence comprising nucleotides of multiples of six is desirably inserted between the transcription end sequence (E) and the transcription start sequence (S) (Calain P. and Roux L., J. Virol., 1993, 67(8), 4822-4830). A foreign gene can be inserted upstream and/or downstream of each of the SeV genes (NP, P, M, F, HN, and L genes). In order not to interfere with the expression of upstream and downstream genes, an E-I-S sequence (transcription end sequence-intervening sequence-transcription start sequence) or a portion of it may be suitably placed upstream or downstream of a foreign gene so that E-I-S sequence is located between each gene. Alternatively, a foreign gene can be expressed by inserting IRES.

Expression level of inserted genes can be regulated by the type of transcription start sequence that is attached to the upstream of the genes. It also can be regulated by the position of insertion and the sequence surrounding the gene. In the SeV, for instance, the closer to the 3'-terminus of the negative strand RNA of the virus genome (the closer to NP gene in the gene arrangement on the wild type virus genome) the insertion position is, the higher the expression level of the inserted gene will be. To achieve a high expression of a foreign gene, it is preferably inserted into the upstream region of the negative stranded genome such as the upstream of the NP gene (3' flanking sequence on the minus strand), or between NP and P genes. Conversely, the closer to the 5'-terminus of the negative strand RNA (the closer to L gene in the gene arrangement on the wild type virus genome) the insertion position is, the lower the expression level of the inserted gene will be. To reduce the expression of a foreign gene, it may be inserted into the most 5' position on the negative strand, that is, downstream of the L gene in the wild type virus genome (5' flanking region of the L gene on the negative strand) or upstream of the L gene (3' flanking region of L gene on the negative strand). Thus, the insertion position of a foreign gene can be properly adjusted so as to obtain a desired expression level of the gene or optimize the combination of the insert with the virus genes surrounding it. For instance, if the overexpression of a gene introduced by a high titer virus vector may cause toxicity, it is possible not only to control the virus titer, but also to reduce the expression level of individual SeV vectors by designing the insertion position closer to the 5'-terminus of the negative strand, or replacing the transcription start sequence with one having lower efficiency so as to obtain an appropriate effect.

Because, in general, it is advantageous in immunity acquisition to obtain high expression of an antigen protein as far as cytotoxicity is not raised, it is preferable to ligate a gene encoding the antigen protein with a highly efficient transcription initiation sequence and to insert the gene into the vicinity of the 3'-terminus of the negative strand genome. Examples of preferable vectors include a vector in which a virus protein of an immunodeficiency virus is encoded at the 3'-side of any virus protein of Paramyxovirus in the negative strand genome of Paramyxovirus vector. For example, a vector in which an antigen gene is inserted upstream (at the 3'-side of the negative strand) of N gene is preferable. Alternatively, an antigen gene may be inserted immediately downstream of N gene.

To help the easy insertion of a foreign gene, a cloning site may be designed at the position of insertion. For example, the cloning site may be the recognition sequence of restriction enzymes. The restriction sites in the virus vector DNA can be used to insert a foreign gene. The cloning site may be a multicloning site that contains recognition sequences for multiple restriction enzymes. The vector used for the vaccine of the present invention may have other foreign genes at positions other than that used for above insertion. Such foreign genes are not limited but may be cytokine or chemokine genes involved in the induction of immunity, or may be other kinds of genes.

Construction of a recombinant Sendai virus vector having a foreign gene can be performed as follows, for example, according to the method described (Hasan, M. K. et al. J. Gen. Virol. 78: 2813-2820, 1997; Yu D. et al., Genes Cells, 1997, 2, 457-466).

First, a DNA sample containing a cDNA sequence encoding a desired foreign gene is prepared. It is preferable that the concentration of the sample is 25 ng/ml or higher and that it can be detected as a single plasmid by electrophoresis. The following description is an example where a foreign gene is inserted into the NotI site of virus genome DNA. If the cDNA sequence contains a NotI site, the site is desirably removed in advance by altering the nucleotide sequence using site-directed mutagenesis and such while maintaining the encoded amino acid sequence. A desired DNA fragment is amplified by PCR from the DNA sample. In order to obtain a fragment having NotI sites at both ends and to add a single copy of the transcription end sequence (E), intervening sequence (I), and transcription start sequence (S) of the Sendai virus (EIS sequence) to one end, a synthesized DNA primer pair, namely, a pair of a forward primer (sense strand) comprising a part of the desired gene, and a reverse primer (antisense) comprising a NotI recognition site, E, I, and S sequences, and part of the desired gene, is prepared.

For example, the forward synthetic DNA sequence contains two or more nucleotides at the 5'-terminus to insure digestion with NotI (preferably 4 nucleotides not containing a sequence derived from the NotI recognition site, such as GCG and GCC; more preferably ACTT). To the 3'-terminus of the sequence, the NotI recognition sequence GCGGCCGC is added. Furthermore, to the 3'-terminus, as a spacer, any 9 nucleotides or those of 9 plus multiples of 6 are added. Furthermore, to the 3'-terminus, a sequence of approximately 25 nucleotides corresponding to the ORF of the desired cDNA starting from the initiation codon ATG is added. The 3'-terminus of the forward synthetic oligo DNA containing approximately 25 nucleotides of the desired cDNA is preferably selected so that the last nucleotide is G or C.

The reverse synthetic DNA sequence contains two or more nucleotides at the 5'-terminus (preferably 4 nucleotides not containing a sequence derived from the NotI recognition site, such as GCG and GCC; more preferably ACTT). To the 3'-terminus of the sequence, the NotI recognition sequence GCGGCCGC is added. Furthermore, to the 3'-terminus, a spacer oligo DNA is added to adjust the length of the primer. The length of the oligo DNA is designed so that it is a multiple of 6 nucleotides including the NotI recognition sequence GCGGCCGC, the sequence complementary to the cDNA, and the EIS sequence derived from the Sendai virus genome as described below (so-called "rule of six"; Kolakofski D. et al., J. Virol., 1998, 72, 891-899; Calain P. and Roux L., J. Virol., 1993, 67, 4822-4830). Furthermore, to the 3'-terminus of the added sequence, complementary sequences to the S sequence of the Sendai virus, preferably 5'-CTTTCACCCT-3' (SEQ ID NO: 1), to the I sequence, preferably 5'-AAG-3', and to the E sequence, preferably 5'-TTTTTCTTACTACGG-3' (SEQ ID NO: 2) are added. Finally, to the 3'-terminus, a sequence, which is selected so that the last nucleotide of the complementary sequence of the desired cDNA becomes G or C, is added, where the last nucleotide is approximately 25 nucleotides upstream from the termination codon. Thus, the 3'-teminus of the reverse synthetic oligo DNA is prepared.

PCR can be performed by a common method using, for example, ExTaq polymerase (TaKaRa). Vent polymerase (NEB) may be used preferably, and the amplified DNA fragment is digested with NotI, and inserted into the NotI site of the plasmid vector pBluescript. The nucleotide sequence of the obtained PCR product is checked with an automated DNA sequencer, and a plasmid having the correct sequence is selected. The insert is excised from the plasmid by NotI digestion, and subcloned into the NotI site of the plasmid containing the Paramyxovirus genomic cDNA. Alternatively, the PCR products may be directly cloned into the NotI site of the latter plasmid to obtain recombinant Sendai virus cDNA.

For example, recombinant Sendai virus genomic cDNA can be constructed according to the methods in the literature (Yu, D. et al., Genes Cells 2: 457-466, 1997; Hasan M. K. et al., J. Gen. Virol., 1997, 78, 2813-2820). For instance, a spacer sequence of 18 by containing the NotI site (5'-(G)-CGGCCGCAGATCTTCACG-3'; SEQ ID NO: 3) is inserted into an adjacent gene locus of a cloned Sendai virus genomic cDNA (pSeV(+)) between the leader sequence and the 5'-terminus of a sequence encoding the N protein, and the plasmid pSeV18+b(+) containing a self-cleavable ribozyme site derived from the antigenomic strand of the delta hepatitis virus is obtained (Hasan M. K. et al., J. General Virol., 1997, 78, 2813-2820). A foreign gene fragment is inserted into the NotI site of pSeV18+b(+) to obtain a recombinant Sendai virus cDNA into which a desired foreign gene has been inserted.

The recombinant Paramyxovirus vector DNA is transcribed in vitro or in cells, and RNP is reconstituted in the presence of L, P, and NP proteins to generate a virus vector comprising the RNP. The present invention provides a method for producing a vaccine comprising the Paramyxovirus vector encoding a virus protein of an immunodeficiency virus, the method comprising transcribing a genomic DNA of the virus. It also provides a DNA for producing the Paramyxovirus vector used as an ingredient of the vaccine of the invention, the DNA comprising the DNA encoding the genome of the virus. The present invention relates to use of DNA encoding the genome of the vector to produce the Paramyxovirus vector used as an ingredient of the vaccine of the invention. Reconstitution of a virus from virus vector DNA can be performed according to the known methods (WO97/16539; WO97/16538; Durbin A. P. et al., Virol., 1997, 235, 323-332; Whelan S. P. et al., Proc. Natl. Acad. Sci. USA, 1995, 92, 8388-8392; Schnell M. J. et al., EMBO J., 1994, 13, 4195-4203; Radecke F. et al., EMBO J., 1995, 14, 5773-5784; Lawson N. D. et al., Proc. Natl. Acad. Sci. USA, 1995, 92, 4477-4481; Garcin D. et al., EMBO J., 1995, 14, 6087-6094; Kato A. et al., Genes Cells, 1996, 1, 569-579; Baron M. D. and Barrett T., J. Virol., 1997, 71; 1265-1271; Bridgen A. and Elliott R. M., Proc. Natl. Acad. Sci. USA, 1996, 93, 15400-15404). These methods enable the reconstitution of Paramyxovirus vectors including the parainfluenza virus, vesicular stomatitis virus, rabies virus, measles virus, rinderpest virus, and Sendai virus vectors from DNA. If the F, HN, and/or M genes are deleted from the virus vector DNA, infective virus particles will not be formed. However, it is possible to generate infective virus particles by introducing these deleted genes and/or genes encoding an envelope protein from another virus into the host cells and expressing them.

Methods for introducing vector DNA into cells may include (1) forming DNA precipitates that can be incorporated into desired cells, (2) making a positively charged complex comprising DNA, a complex that is suitable for incorporation by the desired cells and that has low cytotoxicity, and (3) instantaneously opening a pore large enough for DNA to pass through in the desired plasma membrane using an electrical pulse.

A variety of transfection reagents can be used in (2), for instance, DOTMA (Boehringer), Superfect (QIAGEN #301305), DOTAP, DOPE, and DOSPER (Boehringer #1811169). For (1), transfection using calcium phosphate can be used. In this method, DNA incorporated by cells is taken up into phagocytic vesicles, but it is known that a sufficient amount of DNA is also taken up into the nucleus (Graham F. L. and van Der Eb J., Virol., 1973, 52, 456; Wigler M. and Silverstein S., Cell, 1977, 11, 223). Chen and Okayama studied the optimization of the transfer technology and reported (1) that maximal efficiency is obtained when cells and precipitates are incubated under 2 to 4% CO2 at 35° C. for 15 to 24 hr, (2) that circular DNA has higher activity than linear DNA, and (3) that the optimal precipitates are formed when the DNA concentration in the mixed solution is 20 to 30 mg/ml (Chen C. and Okayama H., Mol. Cell. Biol., 1987, 7, 2745). The method of (2) is suitable for transient transfection. More classically, a transfection method in which DEAE-dextran (Sigma #D-9885 M. W. $5 \times 10^5$) is mixed with DNA at a desired concentration ratio is known. Because most complexes are degraded in the endosome, chloroquine may be added to enhance the transfection efficiency (Calos M. P., Proc. Natl. Acad. Sci. USA, 1983, 80, 3015). The method of (3), called electroporation, may be more broadly applied than the methods of (1) and (2) because it can be used for any kind of cells. The transfection efficiency can be maximized by optimizing the duration of pulse currents, the form of pulse, the strength of the electrical field (gap between electrodes, and voltage), conductivity of buffer, DNA concentration, and cell density.

Among the above three methods, the method of (2) is suitable for introducing a DNA into cells to reconstitute a vector because it is easy to perform and enables the testing of a large number of samples using a large amount of cells. Preferably, transfection reagents such as the Superfect Transfection Reagent (QIAGEN, #301305) or the DOSPER Liposomal Transfection Reagent (Boehringer Mannheim #1811169) are used.

Specific procedures of the reconstitution from cDNA are as follows.

LLC-MK2, a cell line derived from the monkey kidney, is cultured in a 24-well to 6-well plastic plate or in a 100-mm petri dish in minimum essential medium (MEM) containing 10% fetal calf serum (FCS) and an antibiotic (100 units/ml penicillin G and 100 mg/ml streptomycin) to be 70 to 80% confluent. Cells are then infected, for instance, at 2 pfu/cell with recombinant vaccinia virus vTF7-3 that expresses T7 polymerase, which has been inactivated by a 20-minute UV exposure in the presence of 1 mg/ml psoralen (Fuerst T. R. et al., Proc. Natl. Acad. Sci. USA, 1986, 83, 8122-8126; Kato. A. et al., Genes Cells, 1996, 1, 569-579). The amount of psoralen and the duration of UV exposure can be optimized. One hour after infection, cells are transfected by, for example, lipofection using Superfect (QIAGEN) with 2 to 60 mg of, or more preferably 3 to 5 mg of the above recombinant Sendai virus cDNA together with expression plasmids for virus proteins (for example, 24-0.5 mg pGEM-N, 12-0.25 mg pGEM-P, and 24-0.5 mg pGEM-L, or more preferably 1 mg pGEM-N, 0.5 mg pGEM-P, and 1 mg pGEM-L) (Kato. A. et al., Genes Cells, 1996, 1, 569-579) that function in trans and are required for producing a full length Sendai virus genome. The transfected cells are cultured in serum free MEM containing, if desired, 100 mg/ml rifampicin (Sigma) and cytosine arabinoside (AraC) (Sigma) whose concentration is more preferably 40 mg/ml, so that the drug concentration is adjusted to be optimal to minimize the cytotoxicity of the vaccinia virus and maximize the recovery of virus (Kato. A. et al., Genes Cells, 1996, 1, 569-579). Cells are cultured for 48 to 72 hr after transfection, then collected and lysed through three cycles of freeze-thawing. The cell lysates are transfected into LLC-MK2 cells, and after a 3- to 7-day culture, the culture medium is collected. To reconstitute a virus vector lacking a gene encoding an envelope protein that is incapable of replication, the vector may be transfected into LLC-MK2 cells expressing an envelope protein, or co-transfected with expression plasmid for the envelope protein. Alternatively, transfected cells can be overlaid and cultured on LLC-MK2 cells expressing envelope protein to propagate a deletion virus vector (WO00/70055 and WO00/70070). The virus titer of the culture medium can be determined by measuring hemagglutinin activity (HA). The HA may be determined by "endo-point dilution" (Kato. A. et al., Genes Cells, 1996, 1, 569-579; Yonemitsu Y. and Kaneda Y., Hemagglutinating virus of Japan-liposome-mediated gene delivery to vascular cells., Molecular Biology of Vascular Diseases. Methods in Molecular Medicine, Ed. by Baker A. H., Humana Press, 1999, 295-306). The possible contamination of vaccinia virus vTF7-3 can be eliminated by re-amplifying in chicken eggs after the obtained allantoic sample is diluted appropriately ($10^6$ times for instance) and vTF7-3 is removed. Re-amplification may be repeated, for example, three times or more. The obtained virus stock can be stored at −80° C.

Host cells are not limited to any special types of cells as long as the virus vector can be reconstituted in the cells. Host cells may include LLC-MK2 cells, CV-1 cells derived from the monkey kidney, cultured cell lines such as BHK cells derived from hamster kidney, and human-derived cells. To obtain a large quantity of the Sendai virus vector, embryonated chicken eggs may be infected with virus vectors obtained from the above host cells and the vectors can be amplified. The method of producing virus vectors using chicken eggs has been established (Advanced protocols in neuroscience study III, Molecular physiology in neuroscience., Ed. by Nakanishi et al., Kouseisha, Osaka, 1993, 153-172). Specifically, for example, fertilized eggs are incubated for 9 to 12 days at 37 to 38° C. in an incubator to grow the embryos. Virus vectors are inoculated into the allantoic cavity, and eggs are further incubated for several days to propagate the vectors. Conditions such as the duration of incubation may vary depending on the type of recombinant Sendai virus used. Then, the allantoic fluid containing viruses is recovered. Sendai virus vector is separated and purified from the allantoic sample according to the standard method (Tashiro M., Protocols in virus experiments., Ed. by Nagai and Ishihama, MEDICAL VIEW, 1995, 68-73).

For instance, a Sendai virus vector lacking the F protein can be constructed and prepared as follows (WO00/70055 and WO00/70070).

(1) Construction of Sendai Virus Genome cDNA Lacking the F Gene and an Expression Plasmid for F Gene Full length Sendai virus (SeV) genomic cDNA, pSeV18+b(+) (Hasan M. K. et al., J. General Virol., 1997, 78, 2813-2820) (pSeV18+b(+) may be also called pSeV18+), is digested with SphI and KpnI, and the resulting fragment (14673 bp) is recovered and cloned into pUC18 to obtain pUC18/KS. pUC18/KS is used for constructing a region lacking the F gene. Deletion of the F gene is performed by combination of PCR-ligation, and the ORF of the F gene (1698 bp, from ATG to TGA) is replaced with the sequence 5'-atgcatgccggcagatga (SEQ ID NO: 4) in the resulting F gene-deleted SeV genomic cDNA (pSeV18+/DF). PCR products obtained using primers (forward: 5'-gttgagtactgcaagagc/SEQ ID NO: 5; reverse: 5'-tttgccggcatgcatgtttcccaaggggagagtttttgcaacc/ SEQ ID NO: 6) and those with primers (forward: 5'-atgcatgccggcagatga/SEQ ID NO: 7; reverse: 5'-tgggtgaatgagagaat-cagc/SEQ ID NO: 8) are digested with EcoT22I and cloned into the upstream and downstream of the F gene, respectively. The resulting plasmid is digested with SacI and SalI, and the fragment containing the F gene deletion site (4931 bp) is recovered and cloned into pUC18 to obtain pUC18/dFSS. pUC18/dFSS is digested with DraIII, and the fragment recovered is replaced with the DraIII fragment of pSeV18+that contains F gene, and ligated to obtain pSeV18+/DF.

A foreign gene can be inserted into the NsiI or NgoMIV site in the F gene deletion site of pUC18/dFSS. For this purpose, a fragment containing a foreign gene may be amplified using NsiI-tailed primers or NgoMIV-tailed primers.

(2) Preparation of Helper Cells for Inducible Expression of SeV-F Protein

A Cre/loxP inducible expression plasmid for the Sendai virus F gene (SeV-F) is constructed as follows. SeV-F gene is amplified by PCR, and cloned into the unique SwaI site of the pCALNdLw plasmid (Arai et al., J. Virol., 1998, 72, 1115-1121), which is designed for inducible expression of gene products through the function of Cre DNA recombinase, to obtain pCALNdLw/F.

To recover infective virus particles from the F gene-deleted genome, a helper cell line expressing SeV-F protein is established. LLC-MK2 cells, derived from the Simian kidney and commonly used for SeV propagation, may be used. LLC-MK2 cells are cultured at 37° C., 5% CO2 in MEM containing 10% heat-inactivated and immobilized fetal bovine serum (FBS), 50 U/ml of penicillin G sodium, and 50 mg/ml streptomycin. Because of the cytotoxicity of the SeV-F gene product, the gene is cloned into the pCALNdLw, where the expression of a cloned gene is inducible by Cre DNA recombinase. The above pCALNdLw/F is used for transfecting LLC-MK2 cells by the calcium phosphate method (mammalian transfection kit (Stratagene)) according to the standard protocol.

LLC-MK2 cells grown in 10-cm plates to be 40% confluent are transfected with 10 mg pCALNdLw/F and incubated in 10 ml of MEM containing 10% FBS at 37° C. under 5% CO2 for 24 hr. Then, cells are dispersed, resuspended in 10 ml of culture medium, and plated onto five 10-cm dishes, where 5 ml of cell suspension is plated onto one dish, 2 ml onto two, and 0.2 ml onto two. Cells are cultured in 10 ml of MEM containing 10% FBS plus 1200 mg/ml G418 (GIBCO-BRL) for 14 days with medium changed every two days, and stable transfectants are selected. Cells grown in the medium that are resistant to G418 are recovered using cloning rings. Cells of each clone are further cultured until they grow to be 100% confluent in a 10-cm dish.

To induce F protein expression, cells are grown to be 100% confluent in 6 cm dishes, and infected with AxCANCre adenovirus at moi=3 according to the method by Saito et al. (Saito et al., Nucleic Acids Res., 1995, 23, 3816-3821; Arai T. et al., J. Virol., 1998, 72, 1115-1121).

(3) Reconstitution and Propagation of the F Gene-Deleted SeV Virus

The pSeV18+/DF into which a foreign gene has been inserted is transfected into LLC-MK2 cells as follows. Cells are plated at $5\times10^6$ cells/dish onto 100-mm petri dishes, cultured for 24 hr, and then infected at room temperature for 1 hr with the recombinant vaccinia virus that expresses T7 RNA polymerase and that has been treated with psoralen and long UV (365 nm) for 20 min (Fuerst T. R. et al., Proc. Natl. Acad. Sci. USA, 1986, 83, 8122-8126) (moi=2 to 3; preferably moi=2). UV exposure may be performed using UV Stratakinker 2400 equipped with five 15-watt bulbs (catalogue number 400676 (100 V), Stratagene, La Jolla, Calif., USA). After cells are washed three times, plasmids pSeV18+/DF-GFP, pGEM/NP, pGEM/P, and pGEM/L (Kato A. et al., Genes Cells, 1996, 1, 569-579) are resuspended with Opti-MEM (GIBCO) at a ratio of 12 mg/dish, 4 mg/dish, 2 mg/dish, and 4 mg/dish, respectively and mixed with Super-Fect transfection reagent (5 ml SuperFect (QIAGEN) for 1 mg DNA). The mixture is incubated for 10 min at room temperature, then resuspended with 3 ml of OptiMEM with a final concentration of 3% FBS, and added to the cells. After a 3-hr culture in an incubator, cells are washed twice with serum free MEM, and further cultured in MEM containing 40 mg/ml of cytosine β-D-arabinofuranoside (AraC, Sigma) and 7.5 mg/ml of trypsin (GIBCO) for 70 hr. Then, cells are collected and resuspended in OptiMEM at $10^7$ cells/ml. Cells are frozen-thawed three times, then mixed with lipofection reagent DOSPER (Boehringer mannheim) ($10^6$ cells per 25 ml DOSPER), incubated at room temperature for 15 min, and transfected into, for example, LLC-MK2/F7 cells ($10^6$ cells/well in 12-well-plate), which is one of the clones of F gene-expressing helper cells selected as described above. Cells are cultured in serum free MEM containing 40 mg/ml of AraC and 7.5 mg/ml of trypsin, and the culture supernatant is collected. The possible contamination of vaccinia virus can be eliminated by repeating, several times, the procedure in which the obtained supernatant is diluted and used for infection of LLC-MK2 F7 cells and supernatant is recovered.

In preparing deletion virus vectors, two different virus vectors having deletion of a different envelope gene may be transfected into the same cell. In this case, each deleted envelope protein is supplied through expression from the other vector, and this mutual complementation permits the generation of infective virus particles, which can replicate and propagate. Thus, two or more of the virus vectors may be simultaneously inoculated in a combination that complement each other, thereby producing a mixture of each envelope deletion virus vector at a low cost and in a large scale. Because these viruses lacking an envelope gene have a smaller genome, they can allow the insertion of a long foreign gene. In addition, it is difficult for these viruses, which are intrinsically non-infective, to keep the status of co-infection after being diluted outside cells, and thus they are sterilized and less harmful to the environment.

Recovered Paramyxovirus can be purified so as to be substantially pure. Purification can be performed by known purification and separation methods including filtration, centrifugation, column chromatographic purification, and such or a combination of them. The term "substantially pure" used herein means that an isolated substance, for example, compound, polypeptide, virus, and such, occupies a main ratio as a component of the sample in which the substance exists. Typically, a substantially pure component existing in a sample occupies 50% or more, preferably 70% or more, more preferably 80% or more, and even more preferably 90% or more of the whole sample including other components. The ratio is calculated by procedures known to one skilled in the art, for example, as weight-to-weight ratio (w/w). The ration must be calculated by eliminating solvents, salts, added compounds, and such. Specifically, Paramyxovirus can be purified, for example, by a method in which cellulose sulfate ester or crosslinked polysaccharide sulfate ester (Examined Published Japanese Patent Application (JP-B) No. Sho 62-30752; JP-B Sho 62-33879; JP-B Sho 62-30753), a method in which adsorption to fucose sulfate-containing polysaccharide and/or a decomposition product of it (WO97/32010) is used, etc.

Recovered SeV vector can be used as a live recombinant vaccine. Herein, a live vaccine is defined as a composition that enables amplification of vector genome, expression of an antigen antibody, and acquisition of immunity in cells of an individual administered with a virus vector. Because, as shown in Examples, vaccination using SeV vector efficiently induces immunity in a macaque monkey and exhibit no significant clinical symptom, SeV vector can be preferably used. There is no limitation on subjects to which such live vaccine is inoculated and examples of the subjects include all animals that can be infected with an immunodeficiency virus, such as humans, monkeys, cats, dogs, pigs, horses, cattle, etc. In addition, by using above-mentioned SeV vector lacking disseminative capability, a live vaccine that enables vectors not to disseminate can be produced.

In addition, in the case that the expressed protein is incorporated into SeV particles, SeV vector can be used as inactivated whole particle vaccine. Alternatively, an expressed immunodeficiency virus protein that is separated and purified from cells into which SeV vector has been introduced or from SeV vector in the case that the expressed protein is incorporated into SeV particles can be used as vaccine. Purifying an immunodeficiency virus protein from SeV vector is much easier than separating, from whole cell lysate, an immunodeficiency virus protein expressed in cells using, for example, expression vector or the like because SeV vector contains limited kinds of proteins. Known separation techniques can be used for protein purification. For example, using an antibody against an immunodeficiency virus protein, the protein can be purified by immunoaffinity column chromatography. It is expected that frequencies of fever and local reaction after inoculation is repressed by using purified protein as vaccine, compared with live vaccine and inactivated vaccine.

The vaccine containing SeV vector can be combined with a desired, pharmaceutically acceptable carrier or vehicle, if necessary. Herein, a "pharmaceutically acceptable carrier" is defined as those materials that can be administered with a vector, but does not significantly inhibit gene transfer by the vector. For instance, the SeV vector may be appropriately diluted with saline, phosphate buffered saline (PBS), and so on to make a composition. If the SeV vector is propagated in chicken eggs, the composition may contain an allantoic fluid. Also, the vaccine composition containing SeV vector may contain carriers such as deionized water or a 5% dextrose aqueous solution. It may further contain stabilizers, antibiotics, or the like. In addition, preservative and other additives can be added. To raise immunogenicity, immunity accelerating agents such as cytokines, cholera toxin, Salmonella toxin, and the like can be added. Moreover, adjuvants such as alum, incomplete Freund's adjuvant, MF59 (oil emulsion), MTP-PE (muramyl tripeptide derived from *Mycobacterium* cell wall), and QS-21 (derived from soapbark tree *Quilaja saponaria*) can be combined with vaccine.

Vaccination using the vaccine of the present invention can be used for prevention of immunodeficiency virus infection and/or removal of virus or repression of virus propagation after infection. In addition, it can be used for prevention of onset of immunodeficiency syndrome or for treatment after onset. It is also useful for prevention in immunodeficiency virus infection models and/or for the development or evaluation of methods for treating.

The vaccine of the invention may be administered at a sufficient dose so that an effective dose of vectors can be transferred to the cells of the target tissue. Herein, the "effective dose" is defined as a dose that enables the introduction of genes to the cells of the target tissue so as to bring, at least partially, the desired immune response. The administration of an effective dose of the SeV vector containing a desired gene enables the transfected cells to produce the gene product. Preferably, the administration of an effective dose of the SeV vector containing a desired gene may allow the detection of a significant level of expression of the transfected gene in the administered tissue or in blood. A "significant level" is defined as the level at which the expression of the transfected gene (the amount of transcripts or translated products) is detectable. However, the expression level of the transfected gene must be determined by considering its effective level and toxic level.

The expression level of genes transfected into cells can be determined by assays known to those skilled in the art. Transcripts may be detected and quantified by Northern hybridization, RT-PCR, RNA protection assay, and the like. Detection by Northern hybridization, RT-PCR, and such may be performed in situ. To detect translated products, western blot using antibodies, immunoprecipitation, RIA, ELISA, pull down assay, and so on may be used. For an easy detection of transfected gene products, the protein to be expressed may be tagged, or a reporter gene may be contained in the vector. The reporter gene may be that encoding b-galactosidase, CAT, alkaline phosphatase, or GFP, but is not limited to these.

Immune response can be detected by detecting antibodies or immunocytes. For example, assay for humoral immune response to an immunodeficiency virus can be performed by various known assay method, for example, by testing the binding to a virus protein (assay by ELISA, western blotting, etc.), detection of inhibition of syncytium formation, complement fixation, an antibody-dependent cell-mediated cytotoxicity (ADCC) ability, neutralizing capacity for infection or cell fusion, inhibition of interaction between CD4 and gp120, etc.

Cellular immune response can be detected by testing, for example, antigen-specific CTL activity, CTL production, production or activity of helper T cells, and such. In addition, it can be detected by examining cytokines or chemokines produced from activated T cells, such as CD8+ T cells, or other leukocytes. In addition, it can be determined by known lymphocyte proliferation assay, CTL assay, antigen-specific T cell assay, or the like.

Dose of the vector used for administration may vary depending on the disease, the body weight, age, sex, symptom, the purpose of administration, the form and administration method of vaccine, and so on, but it can be appropriately determined by those skilled in the art. The dose of the vector contained in a vaccine may be preferably within the range of approximately $10^5$ pfu/ml to $10^{11}$ pfu/ml, and more preferably approximately $10^7$ pfu/ml to $10^9$ pfu/ml, but most preferably, the vector is administered at approximately $1 \times 10^8$ pfu/ml to $5 \times 10^8$ pfu/ml with pharmaceutically acceptable carriers.

Vaccine can be inoculated intradermally, subdermally, intranasally, transbronchially, intramuscularly, intravenously, or orally. For example, vaccine inoculation to the vicinity of upper respiratory tract, namely, to intranasal mucous membrane and upper respiratory tract can induce mucous immunity. To achieve this, it is effective to inoculate SeV vaccine to respiratory tract by intranasal spray and such. Intranasal administration can be also performed, for example, by administration mediating a catheter. In addition, cells into which SeV has been introduced can be inoculated as vaccine. For example, cells derived from an individual to which vaccine is to be inoculated are infected with SeV, and then, vaccination is carried out by ex vivo administration.

Furthermore, it is effective to induce sufficient immunity not only by single dose administration but also by, for example, double or multiple dose administration. In the case of humans, the interval of multiple dose administration is usually two to four weeks.

In multiple dose administration, vaccine of the present invention containing SeV can be administered multiple times, but it is also preferable to use a combination of SeV vaccine with other vaccines. As described above, one demerit of viral vector-based vaccine strategies is the induction of vigorous immune responses against the vector virus-derived antigens rather than the target antigens. This problem can be solved by using two or more different kinds of viral vectors for priming and boosting, respectively. Therefore, as described above, DNA vaccine-based priming followed by viral vector-based boosting is also a favorable strategy. In addition, re-inoculation of the same recombinant virus could be insufficient for boosting antigen-specific responses. It is thus also feasible to prime with a vaccine by SeV vector and boost with a different viral vector, or a DNA vaccine (Amara, R. R. et al., Science, 8 Mar. 2001, 10.1126/science.1058915). In addition, expression of multiple antigens using recombinant SeV vectors can improve the protective efficacy.

Thus, there is no limitation on vaccines combined with SeV vaccine in prime-boost protocol using different kinds of vaccines and desired vaccine can be used. Examples include recombinant subunit vaccine, live recombinant vaccine based on a virus except SeV or a microorganism, whole particle inactivated immunodeficiency virus, pseudovirion or virus-like particle of immunodeficiency virus, peptide vaccine, live vaccine of attenuated immunodeficiency virus, DNA vaccine, and such, but are not limited thereto. Subunit vaccine is defined as a vaccine that has not all antigens derived from target immunodeficiency virus and that contains one or more selected protein antigens. Such vaccine is at least partially separated from the other components of the virus or the components derived from infected cells. Subunit vaccine can be prepared by at least partially purifying immunodeficiency virus proteins. In addition it can be generated by production using recombination or by synthesis. Examples of viruses or microorganisms used as a base of live recombinant vaccine include poxvirus, adenovirus, Salmonella, poliovirus, *Mycobacterium,* influenza virus, Semliki forest virus, and such, but are not limited thereto. Booster immunization can be performed by using, as an immunodeficiency virus, a combination of the vaccine of the present invention with confined replicative virus whose replication ability is confined by substitution of env gene (Matano, T. et al. 2000. Vaccine 18: 3310-3318). There is no limitation on the order of inoculation of SeV vaccine and other vaccines. After SeV vaccine is inoculated, other vaccines can be inoculated, and oppositely, after other vaccines are inoculated, SeV vaccine can be inoculated.

For example, after priming is performed with DNA vaccine, boost is performed with SeV vaccine. Such vaccination is a method comprising the steps of (a) administering a DNA vaccine and then (b) administering a Paramyxovirus vector encoding a virus protein of an immunodeficiency virus. As a DNA vaccine, DNA encoding, for example, immunodeficiency virus genome can be used. DNA vaccine can be inoculated, for example, by intramuscular administration and/or gene gun administration. For example, after DNA vaccine is inoculated several times, vaccine based on SeV of the present invention can be inoculated. The interval of inoculation is usually several days to several weeks.

Examples of animals to which vaccine can be inoculated include all hosts that have immune system and that can be infected with an immunodeficiency virus and include all mammalian animals and such including humans, monkeys, mice, rats, rabbits, sheep, pigs, cattle, horses, birds, and such. Examples of animals to which vaccine of the present invention preferably include primates. Examples of primates that can be subjects of inoculation of the vaccine of the present invention except humans (non-human primates) include prosimians such as lemur, loris, tarsier and the like; anthropoids such as platyrrhini and catarrhini; and apes such as gibbon, orangutan, gorilla, chimpanzee, bonobo, etc. Examples of catarrhini include, in particular, Cercopithecoidea, specifically the genus *Macaca* including Japanese macaque, cynomolgus macaque, rhesus monkey, bonnet monkey, pig-tailed macaque, brown stump-tailed macaque, Assam monkey, etc. Inoculation of vaccines to non-human primates is extremely useful for development and evaluation of an AIDS vaccine aimed at clinical application to humans.

Vaccine containing SeV vector encoding a virus protein of an immunodeficiency virus can locally and systemically induce the immune response of a host. In particular, a cell into which the vector is introduced functions as a stimulator cell of antigen-specific immune response and induces cellular immune response. The present invention provides a method for inducing cellular immune response specific to a virus protein of an immunodeficiency virus, the method comprising the steps of (a) introducing a Sendai virus vector encoding a virus protein of an immunodeficiency virus into an antigen presenting cell and (b) contacting the antigen presenting cell with a T helper cell and a cytotoxic T cell. Herein, "contacting" a cell also includes allowing cells to contact with each other. In other words, it includes letting cells to contact with each other, for example, injecting, into blood, cells into which vectors are introduced (the cells can contact with T helper cells and cytotoxic T cells in a living body); co-culturing cells into which vectors are introduced, T helper cells, and cytotoxic T cells in the same medium; etc. In addition, antigen-specific "cellular immune response induction" means at least a part of induction in the process of the cellular immune response. For example, it means stimulation of antigen-specific CTL, increase of frequency and activity (for example, cytotoxicity) of the CTL, etc.

An antigen presenting cell means a cell on which major histocompatibility complex (MHC) class I or MHC class II is presented and that has an ability to bind a peptide of an antigen protein to each cell. Examples of antigen presenting cells include dendritic cell (DC). MHC class I molecule is a molecule binding to antigen peptide and presenting it to cytotoxic T cells (CD8+). MHC class II molecule is a molecule binding to antigen peptide and presenting it to cytotoxic T cells (CD4+). T helper cell means a group of T cell family and is a cell recognizing an antigen presented by MHC class II molecule and organizing the cascade of immune response. Cytotoxic T cell means a group of T cell family and is a cell recognizing an antigen presented by MHC class I molecule and killing cells such as virus-infected cells, cancers, grafts, and such (Xu Met al., Trends Biotechnol. 18(4): 167-72, 2000).

For example, by introducing SeV vector encoding a virus protein of an immunodeficiency virus into peripheral blood mononuclear cell (PBMC) and such and by co-culturing in vitro with PBMC, cellular immune response such as induction of IFM-γ production and propagation of virus protein-specific CTL of an immunodeficiency virus can be induced. In addition, in vivo administration enables induction of antigen-specific cellular immune response in a host.

Cellular immune response can be confirmed, for example, by assay for the amount of IFN-γ and frequency measurement for CD8+ IFN-γ+ T cell. In addition, CTL activity can be also assayed by using, as targets, cells in which virus proteins of an immnodeficiency virus are expressed and by measuring the lysis of target cells. Such target cells can be prepared by introducing the above-mentioned SeV vector. For example, SeV expressing a virus protein of an immunodeficiency virus is introduced into autologous *Herpesvirus papio* immortalized B lymphoblast cell strain (BLC) or the like. The cells are incubated with a sample expected to contain CTL, and the lysis of the BLC can be measured with $^{51}$Cr release and the like as an index. In addition, immortalized cell strain H9 (derived from human T cell) and the like can be exemplified.

The present invention relates to use of SeV vector encoding a virus protein of an immunodeficiency virus or a cell into which the vector is introduced for inducing or detecting cellular immune response specific to a virus protein of an immunodeficiency virus. In addition, the present invention relates to a stimulator cell of cellular immune response specific to a virus protein of an immunodeficiency virus, the stimulator cell including a cell into which SeV vector encoding a virus protein of an immunodeficiency virus is introduced. Moreover, the present invention relates to a target cell of cellular immune response specific to a virus protein of an immunodeficiency virus, the target cell including a cell into which SeV vector encoding a virus protein of an immunodeficiency virus is introduced. In addition, the present invention relates to use of SeV vector encoding a virus protein of an immunodeficiency virus for expressing a virus protein of an immunodeficiency virus in the stimulator cell or the target cell.

There is no limitation on a virus protein of an immunodeficiency virus encoded by SeV vector. As shown above, they may be virus structural proteins, regulatory proteins, accessory proteins, etc. Examples of the structural proteins include Gag, Pol, Env, etc. For example, using SeV encoding Gag protein of an immunodeficiency virus, Gag-specific cellular immune response can be induced.

The present invention provides a vaccine containing a Sendai virus vector encoding a virus protein of an immunodeficiency virus. Sendai virus enables safe and easy production of live recombinant vaccine because the virus has low toxicity and a large amount of it can be produced using chicken eggs. The vaccine of the present invention provides promising vaccine strategy that represses the infection of AIDS virus and/or the onset and progress of AIDS.

The present invention is illustrated in detail below with reference to examples, but it is not to be construed as being limited thereto. All the references cited herein are incorporated by reference.

EXAMPLE 1

SeV/SIVgag Collection

By using a safer V knock-out version of SeV (V[−]SeV) (Kato, A. et al. 1997. *J. Virol.* 71:7266-7272; Kato, A. et al. 1997. *EMBO J.* 16:578-587), we constructed a recombinant SeV vector expressing SIV Gag, SeV/SIVgag. Knock-out of the V gene, an accessory gene in SeV, by recombinant technology remarkably attenuated SeV pathogenicity for mice without disturbing viral gene expression and replication in cultured cells. A plasmid, pSeV(+)18bV(−), containing a full length of the attenuated V-defective SeV genome cDNA was described before (Kato, A. et al. 1996. *Genes Cells* 1:569-579; Hasan, M. K. et al. 1997. *J. Gen. Virol.* 78:2813-2820). A gene fragment encoding SIVmac239 Gag (nucleotides 1306 to 2845 [GenBank accession number: M33262] (Kestler, H. et al. 1990. *Science* 248:1109-1112)) was prepared by PCR amplification and introduced into pSeV(+)18bV(−) to obtain pSeV(+)18bV(−)/SIVgag. Primers used for the PCR are 5'-AAG CGG CCG CGA GAT GGG CGT GAG AAA CTC CG-3' (SEQ ID NO: 9) and 5'-TTG CGG CCG CGA TGA ACT TTC ACC CTA AGT TTT TCT TAC TGT GAC TAC TGG TCT CCT CCA AAG-3' (SEQ ID NO: 10). The gag gene fragment was inserted into the NotI site, immediately upstream of N coding region, in pSeV(+)18bV(−) (FIG. 1A). This plasmid pSeV(+)18bV(−)/SIVgag generates a full length of SeV/SIVgag antigenomic RNA in the presence of T7 RNA polymerase. The recombinant SeV, SeV/SIVgag, was recovered from pSeV(+)18bV(−)/SIVgag as described (Kato, A. et al. 1996. *Genes Cells* 1:569-579). Specifically, LLCMK2 cells were infected with vTF7-3, which is a recombinant vaccinia virus (VV) vector expressing T7 RNA polymerase (Fuerst, T. R. et al., 1986, Proc. Natl. Acad. Sci. USA 83: 8122-8126), and pSeV(+)18bV(−)/SIVgag, pGEM-N, pGEM-P, and pGEM-L (Garcin, D. et al., 1995, EMBO J. 14: 6087-6094) were cotransfected. Cells were collected 40 hours after transfection and injected into allantoic cavity of chicken eggs. After 2 passages, allantoic fluid was collected to be used as SeV/SIVgag. A control SeV, SeV/control, was similarly obtained from pSeV(+)18bV(−). The SeV titer (CIU [cell infectious unit]/ml) was assayed on CV1 cells by immunostaining using an anti-SeV-antibody as described (Kiyotani, K. et al. 1990. *Virology* 177:65-74).

EXAMPLE 2

SIV Gag-Expression Using SeV/SIVgag In Vitro

Infectious SeV/SIVgag was rescued from the plasmid, pSeV(+)18bV(−)/SIVgag (FIG. 1A), according to a standard transfection protocol (see Example 1). Cells were infected with this SeV/SIVgag, and the expressed proteins were analyzed as follows. For harvesting cell lysates, CV-1 cells were seeded at a density of $4\times10^5$ cells per well in 6-well plate, grown overnight, and then infected with SeV/control or SeV/SIVgag at m.o.i. of 5. One day later, the cells were lysed with 600 μl of lysis buffer (50 mM Tris-HCl, pH 8.0, 150 mM NaCl, 0.02% sodium azide, 0.1% sodium dodecyl sulfate, 0.5% sodium deoxycholate, 0.1 mg/ml phenylmethylsulfonyl fluoride, 1% Triton X-100). For each lane, 10 μl of cell lysate was loaded. Western blot analysis using a monoclonal mouse anti-p27 antibody was performed as described (Matano, T. et al. 1993. *J. Virol.* 67:2026-2033). Immunostaining was performed by using the anti-p27 antibody and a fluorescein-conjugated goat anti-mouse immunoglobulin G (IgG) antibody as described (Matano, T. et al. 1993. *J. Virol.* 67:2026-2033). Expression of unprocessed SIV Gag, p55, in SeV/SIVgag-infected CV1 cells was confirmed by Western blotting as well as by immunostaining using a monoclonal anti-SIV Gag p27 antibody (FIG. 1B and FIG. 1C). The recombinant virus showed slightly slower proliferation kinetics compared with the SeV/control (FIG. 1D). This retarded proliferation might be due to the increase in genome length (SeV/control, 15.4 kb; SeV/SIVgag, 17.0 kb) (Yu, D. et al. 1997. *Genes Cells* 2:457-466; Hasan, M. K. et al. 1997. *J. Gen. Virol.* 78:2813-2820; Sakai, Y. et al. 1999. *FEBS Lett.* 456: 221-226).

EXAMPLE 3

Induction of SIV Gag-Specific Cellular Response by SeV/SIVgag In Vitro

To examine whether SIV Gag-specific response is induced by SeV/SIVgag-mediated Gag expression, cellular immune response was tested in vitro using PBMC prepared from a rhesus macaque (Macaca mulatta). This rhesus macaque was previously vaccinated with a naked DNA expressing SIV antigens (a plasmid DNA expressing SIV antigen including Gag) and challenged with SIVmac239 for other experiments. The SIVmac239 challenge stock was prepared on rhesus macaque PBMC as described before (Kestler, H. et al., 1990, Science 248: 1109-1112; Shibata, R. et al., 1997, J. Infect. Dis. 176: 362-373). The infectious titer of the stock was assayed on MT-4 cells. These rhesus macaques were tested negative for SeV, SIV, and simian type D retrovirus before use and maintained in accordance with the institutional guideline for laboratory animals. Blood collection, vaccination, and virus inoculations were performed under ketamine anesthesia.

The PBMC freshly prepared from the rhesus macaque on week 3 after the SIV challenge were used as the effector in this CTL assay. Peripheral blood mononuclear cells (PBMC) were prepared from the whole blood sample as described before (Shibata, R. et al., 1997, J. Infect. Dis. 176: 362-373). PBMC were cultured in RPMI1640 (Life Technologies) with 10% fetal bovine serum (Hyclone). PBMC were infected with SeV/control or SeV/SIVgag at MOI of 10, incubated for 2 hrs, and used for the coculture. SIV Gag-specific stimulation cocultures were initiated by mixing $5\times10^5$ PBMC with $1\times10^5$ SeV/SIVgag-infected PBMC per well in 96-well U-bottom plate, and non-specific stimulation cocultures by mixing $5\times10^5$ PBMC with $1\times10^5$ SeV/control-infected PBMC. After 3-day cocultivation, the culture supernatant was harvested and cells were cultured in the medium containing 10 unit/ml of recombinant human interleukin-2 (Boehringer Mannheim). Interferon-γ (IFN-γ) concentration in the supernatant was examined by enzyme-linked immunosorbent assay (ELISA) (Biosource). The lower limit of detection in this assay is 15 pg/ml. The PBMC in the SIV Gag-specific stimulation coculture were used as effector cells in cytotoxic T lymphocyte (CTL) assay. Alternatively, freshly prepared PBMC were used as effector. The CTL assay ($^{51}$Cr-release assay) was performed as described before (Voss, Q. et al., 1992, J. Virol. Methods 39: 185-195; Voss, Q. et al., 1995, Virology 208: 770-775). The autologous *Herpesvirus papio*-immortalized B-lymphoblastoid cell line (B-LCL) infected with a recombinant VV expressing SIV Gag, VV/SIVgag, was used as the target for SIV Gag-specific lysis. Alternatively, SeV/SIVgag-infected B-LCL was used. The B-LCL infected with a control VV (VV/WR) or SeV/control was used for non-specific lysis. The percent $^{51}$Cr-release is calculated as follows: % $^{51}$Cr release=(test release−spontaneous release)/(maximum release−spontaneous release)×100. Then, the percent Gag specific $^{51}$Cr-release is calculated by subtracting the percent $^{51}$Cr-release in non-specific lysis from that in Gag-specific lysis. Gag-specific CTL activity is considered positive when the percent Gag-specific $^{51}$Cr-release is exceeding 10%.

Figure 2:
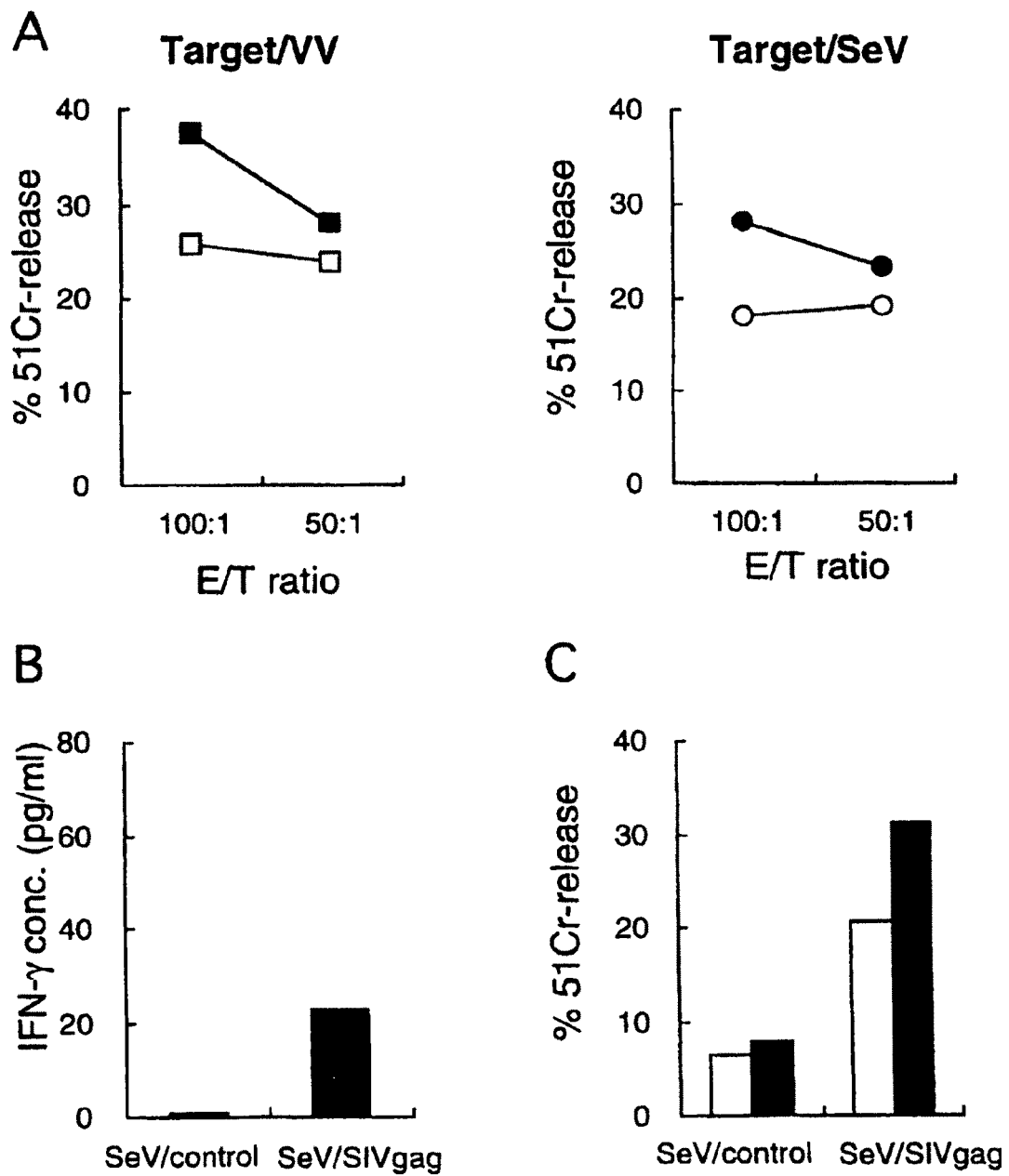
FIG. 2 shows SIV Gag-specific cellular immune responses induced by SeV/SIVgag-mediated Gag expression. (A) CTL assay using B cells infected with VV/SIVgag (left panel, closed square) or SeV/SIVgag (right panel, closed circle) as the target for SIV Gag-specific lysis. B cells infected with VV/WR (left panel, open square) or SeV/control (right panel, open circle) were used for non-specific lysis. Fresh Rh018 PBMC sampled on week 3 after SIV infection were used as the effector. (B) IFN-γ production in PBMC coculture with SeV/SIVgag-infected cells. Rh018 PBMC sampled on week were used for the non-specific stimulation coculture with SeV/control-infected cells (left lane) and the Gag-specific stimulation coculture with SeV/SIVgag-infected cells (right lane). IFN-γ concentration in their supernatant was assayed by ELISA. (C) SIV Gag-specific CTL expansion in PBMC coculture with SeV/SIVgag-infected cells. PBMC in the non-specific (left lanes) or the Gag-specific stimulation coculture (right lanes) described above were used as the effector. VV/SIVgag-infected B cells were used as the target for Gag-specific lysis (closed box) and VV/WR-infected B cells for non-specific lysis (open box).

The autologous B-LCL infected with SeV/SIVgag or VV/SIVgag was used as the target. As shown in FIG. 2A, Gag-specific lysis was observed in the assay using the SeV/SIVgag-infected B-LCL as well as that using the VV/SIVgag-infected B-LCL, indicating that SeV/SIVgag-infected B-LCL worked as an SIV Gag-specific CTL target.

Next, we examined whether SeV/SIVgag-infected cells would induce SIV Gag-specific CTL expansion. Coculture of PBMC prepared from the rhesus macaque Rh018 on week 12 with the SeV/SIVgag-infected PBMC resulted in the production of IFN-γ, a Th1 cytokine (FIG. 2B). In contrast, no detectable IFN-γ was induced by the PBMC coculture with the SeV/control-infected PBMC. SIV Gag-specific CTL activity was found in the former coculture (coculture with SeV/SIVgag-infected PBMC) but not in the latter control. coculture (coculture with SeV/control-infected PBMC) (FIG. 2C), indicating Gag-specific CTL expansion by the SeV/SIVgag-infected cells.

EXAMPLE 4

SeV/SIVgag-Vaccination in Cynomolgus Macaques

Figure 3:
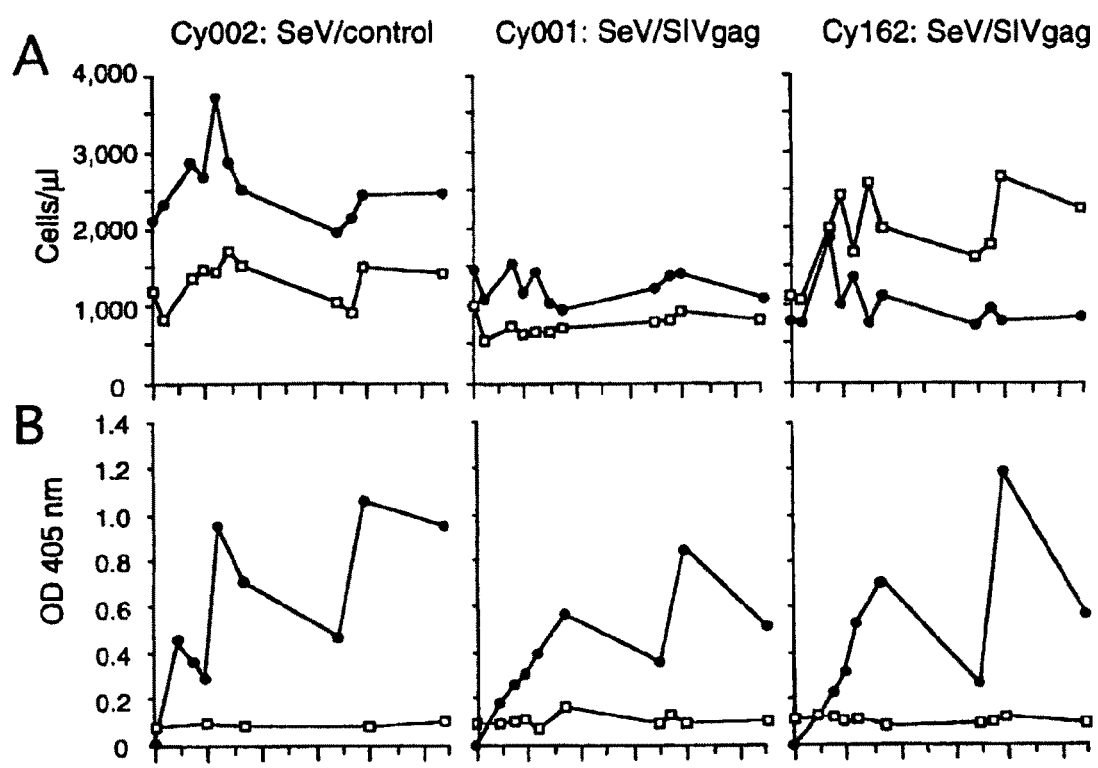
FIG. 3 shows immune responses after the vaccination. The arrows represent the time points of the first, the second, and the third vaccinations. (A) CD4-positive (closed circle) or CD8-positive (open square) lymphocyte numbers in peripheral blood (cells/μl). (B) Optical densities (OD) at 405 nm in anti-SeV (closed circle) or anti-p27 (open square) antibody ELISA.

Vaccination experiments were performed using four cynomolgus macaques (*Macaca fascicularis*) according to the protocol summarized in Table 1. Four cynomolgus macaques were tested negative for SeV, SIV and simian type D retrovirus before use and maintained in accordance with the institutional guideline for laboratory animals. Blood collection, sampling of nasal swab, vaccination, and virus inoculations were performed under ketamine anesthesia. Cynomolgus macaque 1329605029 (Cy029) received no vaccination and was used as a naive control. Cynomolgus macaque 1429407002 (Cy002) received a control vaccination, intranasal SeV/control inoculation of $10^8$ CIU, three times on weeks 0, 4 and 14 after the first immunization. On the same schedule, two cynomolgus macaques, 1129307001 (Cy001) and 1128206162 (Cy162), were vaccinated intranasally with SeV/SIVgag of $10^8$ CIU three times. None of the cynomolgus macaques showed pathological signs including body weight loss alter the vaccination. No significant decrease in peripheral CD4 nor CD8 cell number was observed, either (FIG. 3A).

SeV/SIVgag replication and expression in the respiratory tracts were examined with the nasal swabs (Table 1). Sampling of nasal swab was performed as described before (Hurwitz, J. L. et al., 1997, Vaccine 15: 533-540). The swab sample was diluted in medium and injected into the allantoic cavity of chicken eggs for recovery of SeV. After 48-hr incubation, the allantoic fluid was harvested and subjected to hemagglutination (HA) assay to detect SeV. To examine SIV gag-expression, RNA was extracted from the swab sample by using High Pure Viral RNA kit (Boehringer Mannheim). Nested RT-PCR was performed by using SIV gag-specific primers. The primers used for the first RT-PCR are 5'-AGA AAC TCC GTC TTG TCA GG-3' (SEQ ID NO: 11) and 5'-TGA TAA TCT GCA TAG CCG C-3' (SEQ ID NO: 12), and the primers for the second PCR are 5'-GAT TAG CAG AAA GCC TGT TGG-3' (SEQ ID NO: 13) and 5'-TGC AAC CTT CTG ACA GTG C-3' (SEQ ID NO: 14).

In cynomolgus macaques Cy002, Cy001, and Cy162, SeV (SeV/control or SeV/SIVgag) replication was detected on week 1 as evidenced by SeV HA activities accumulating in the allantoic fluid of chicken eggs inoculated with the swab (Table 1). No detectable SeV was recovered on week 2. Neither the second nor the third vaccination resulted in detectable SeV in the swabs, either. By nested PCR using SIV gag-specific primers, SIV gag-expression was detected in the nasal swab in both of the SeV/SIVgag-vaccinated cynomolgus macaques (Cy001 and Cy162) but not in the SeV/control-vaccinated cynomolgus macaque (Cy002) (Table 1).

Immune responses after the vaccination were investigated in these three cynomolgus macaques. Examination of humoral immune responses by ELISA showed a high level induction of plasma anti-SeV antibody in all three cynomolgus macaques (FIG. 3B). The second and the third vaccinations induced rapid increases in their levels, suggesting the boosting effect. On the contrary, no significant induction of plasma anti-SIV Gag p27 antibody was observed. Anti-SeV antibody ELISA was performed by using disrupted SeV. Anti-SIV Gag p27 antibody ELISA was performed by using a recombinant p27 antigen (ImmunoDiagnostics). The plasma samples were diluted by 1000-fold for the anti-SeV antibody ELISA and by 100-fold for the anti-p27 antibody ELISA.

One naive cynomolgus macaque (Cy029), one SeV/control-vaccinated cynomolgus macaque (Cy002), and two SeV/SIVgag-vaccinated cynomolgus macaques (Cy001 and Cy162) were challenged intravenously with a large dose (100 TCID50) of SIVmac239 on week 22. Specifically, the two cynomolgus macaques were intranasally vaccinated with $10^8$

TABLE 1

Vaccination protocol and SeV/SIVgag expression in vivo

| Cynomolgus macaques | Vaccination | Expression | Wks after the initial vaccination | | | | | | | |
|---|---|---|---|---|---|---|---|---|---|---|
| | | | 0 | 1 | 2 | 4 | 5 | 14 | 15 | 22 |
| | | | 1st SeV | | | 2nd SeV | | 3rd SeV | | |
| Cy002 | SeV/control $10^8$ CIU IN | SeV gag | − − | + − | − − | − − | − ND | − ND | − ND | ND − |
| Cy001 | SeV/SIVgag $10^8$ CIU IN | SeV gag | − − | + + | + − | − − | − + | − − | − + | ND − |
| Cy162 | SeV/SIVgag $10^8$ CIU IN | SeV gag | − − | + + | − + | − − | − + | − − | − − | ND − |

ND not determined

CIU SeV/SIVgag three times (weeks 0, 4, and 14). Twenty-two weeks after the first vaccination, these cynomolgus macaques were intravenously challenged with 100 TCID50 of SIVmac239 and SIV RNA in plasma was measured. The SeV/control-vaccinated cynomolgus macaque and the naive cynomolgus macaque were used as controls.

The plasma SIV RNA amounts of these cynomolgus macaques were measured as follows. Plasma RNA was extracted using High Pure Viral RNA kit. Nested PCR was performed by using SIV env-specific primers. The primers used for the first RT-PCR are 5'-ATG GGA TGT CTT GGG AAT C-3' (SEQ ID NO: 15) and 5'-CCA AAT CTG CAG AGT ACC AAG-3' (SEQ ID NO: 16), and the primers for the second PCR are 5'-CAG CTT GGA GGA ATG CG-3' (SEQ ID NO: 17) and 5'-CTT GTT CCA AGC CTG TGC-3' (SEQ ID NO: 18). Five-fold dilutions of RNA samples were amplified in quadruplicate for quantification as described before (Shibata, R. et al., 1997, J. Infect. Dis. 176: 362-373; Reed, L. J. and Muench, H., 1938, Am. J. Hyg. 27: 493-497). The lower limit of detection in this assay is $1.0 \times 10^2$ copies/ma.

Figure 4:
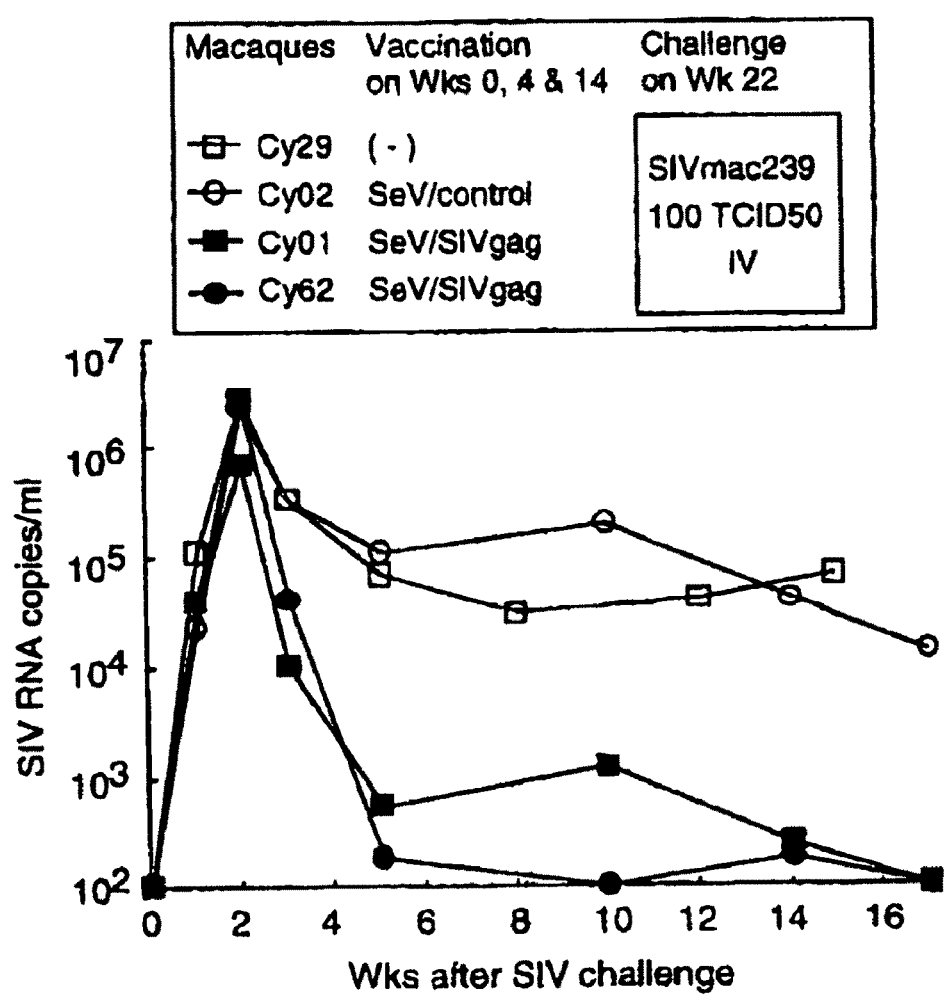
FIG. 4 shows plasma SIV RNA copy numbers (copies/ml) after SIV challenge. Cynomolgus macaques were vaccinated with 10$^8$ CIU of SeV vectors three times by intranasal inoculation. The cynomolgus macaques were challenged intravenously with 100 TCID50 of SIVmac239 on week 22 after the initial vaccination.

All the four cynomolgus macaques showed a similar level of plasma SIV load peaking at week 2 after the challenge (FIG. 4). Thereafter, the plasma SIV RNA level decreased but remained at about $10^5$ copies/ml in both the control cynomolgus macaques. In contrast, the initial viremia was followed by significantly lower viral loads ($10^2$ to $10^3$ copies/ml) in both the SeV/SIVgag-vaccinated cynomolgus macaques. More notable the plasma viral loads in the immunized cynomolgus macaques eventually became below the detectable level (100 copies/ml), while those in the control cynomolgus macaques remained as high as around $10^5$ copies/ml (FIG. 4).

EXAMPLE 5

SeV/SIVgag Expression in Each Tissue in Cynomolgus Macaques

To examine the primary replication of the recombinant SeV in cynomolgus macaques, six cynomolgus macaques were inoculated intranasally with SeV/SIVgag (Table 2, Group I). Cynomolgus macaques were maintained in accordance with the institutional guideline for laboratory animals. These macaques were tested negative for SeV and SIV before use. Blood collection, sampling of nasal swab, and vaccination were performed under ketamine anesthesia. None of them showed apparent clinical symptom after the inoculation. Two of them in group I-A (C3880 and C4325) were euthanized at day 4, two in group I-B (C3993 and C4240) at day 7, and two in group I-C (C3882 and C4324) at day 13 after the inoculation, respectively. Cells were prepared from each tissue taken at autopsy, and RNA was extracted from the cells.

From LN, the thymus, and the spleen, cells were prepared by mincing the tissues. From the nasal mucosa, the palatine tonsil, the trachea, and the lung, cells were prepared after treatment with collagenase and dispase. These cells were washed with PBS three times before the RNA extraction. Peripheral blood mononuclear cells (PBMC) were prepared from the whole blood samples by using Ficoll-Paque Plus (Amersham-Pharmacia Biotech) as described (Shibata, R. et al. 1997. *J. Infect. Dis.* 176:362-373). RNA was extracted from the cells by using a RNA-extraction kit (Qiagen). Nested RT-PCR (reverse transcription and nested PCR) was performed by using SIV gag-specific primers and the gag RNA level was quantified by limiting dilution of the RNA sample to determine the end-point as described (Shibata, R. et al. 1997. *J. Infect. Dis.* 176:362-373). SeV N mRNA level was quantified by a quantitative PCR using TaqMan PCR system (ABI PRISM 7700, Applied Biosystems Japan).

TABLE 2

Animal protocols

| Group | Macaques | Vaccination inoculum[a] | Autopsy |
|---|---|---|---|
| I-A | C3880 | SeV/SIVgag | at day 4 |
|  | C4325 | SeV/SIVgag | at day 4 |
| I-B | C3993 | SeV/SIVgag | at day 7 |
|  | C4240 | SeV/SIVgag | at day 7 |
| I-C | C3882 | SeV/SIVgag | at day 13 |
|  | C4324 | SeV/SIVgag | at day 13 |
| II-A | R010 | SeV/control | ND[b] |
|  | R014 | SeV/control | ND |
| II-B | R013 | SeV/SIVgag | ND |
|  | R015 | SeV/SIVgag | ND |
|  | R017 | SeV/SIVgag | ND |

Figure 5:
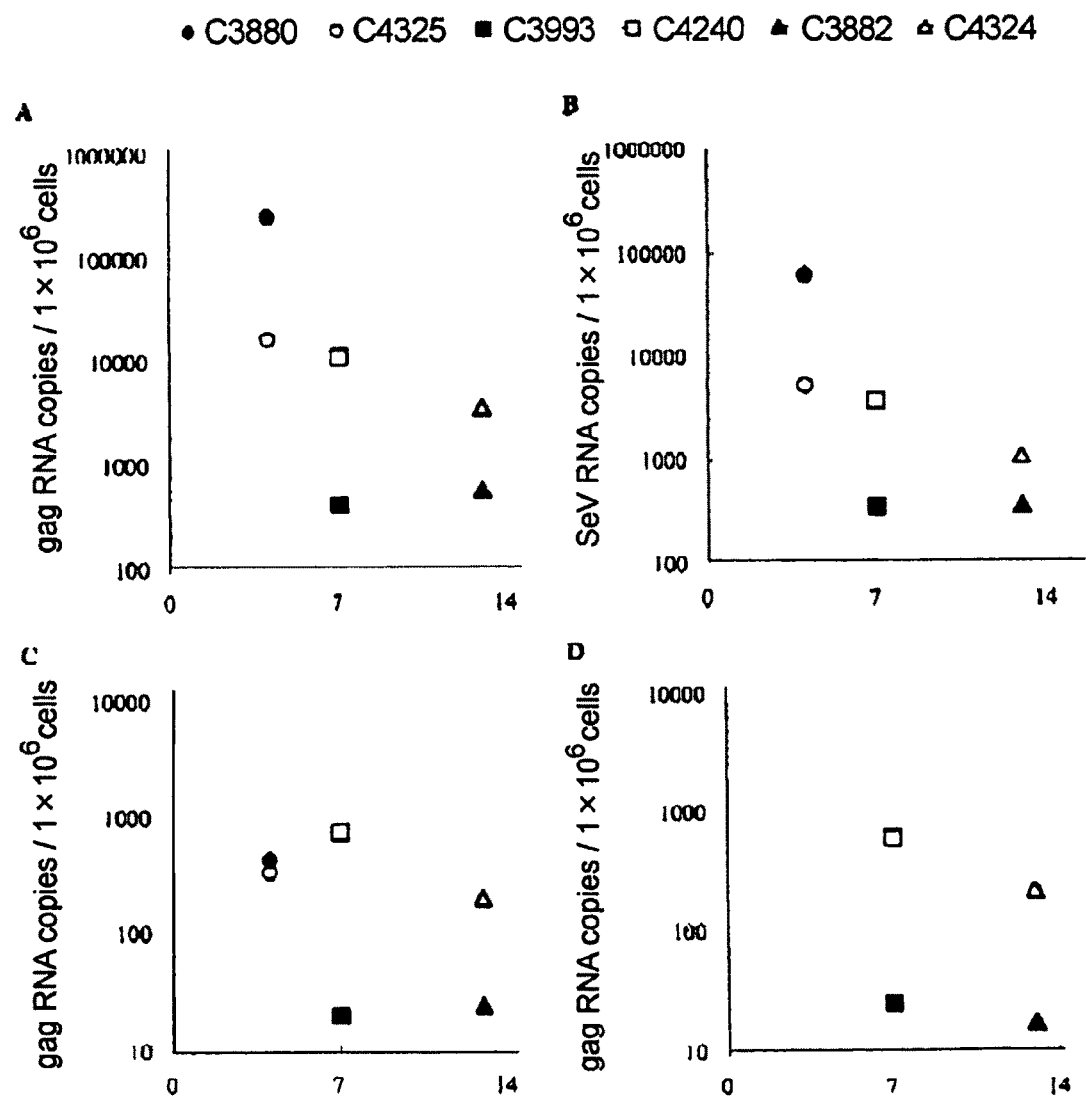
FIG. 5 shows SeV/SIVgag RNA expression in the group I cynomolgus macaques. (A) SIV gag RNA level in the cells prepared from the nasal mucosa. (B) SeV N mRNA level in the cells prepared from the nasal mucosa. (C) SIV gag RNA level in the cells prepared from the retropharyngeal LN. (D) SIV gag RNA level in the cells prepared from the submandibular LN. The level in C3880 or C4325 at day 4 was not determined.

[a] $10^8$ CIU of SeV/control or SeV/SIVgag was inoculated intranasally.
[b] not done 5-1. SeV/SIVgag Expression in the Nasal Mucosa in Cynomolgus Macaques By a quantitative RT-PCR, significant level of SIV gag RNA was detected in the cells prepared from the nasal mucosa in all the six cynomolgus macaques (FIG. 5A). About $1.7 \times 10^4$ or $2.6 \times 10^5$ copies of gag RNA per $10^6$ cells were detected at day 4 in group I-A. The expression levels at day 7 and at 13 were less than those at day 4. Further, the SeV N mRNA expression level in the nasal mucosa was detected by a quantitative RT-PCR (FIG. 5B). The SeV N mRNA level (shown in FIG. 5B) corresponded to ¼ or ⅓ of the gag RNA level (shown in FIG. 5A) in most of the cynomolgus macaques. These results confirmed significant SeV/SIVgag expression in the nasal mucosa in SeV/SIVgag-inoculated cynomolgus macaques.

Then, we examined if SeV could be recovered from the nasal swab. The nasal swab was collected as described above. The nasal swab sample was diluted in RPMI-1640 and injected into the allantoic cavity of chicken eggs for recovery of SeV. In case of SeV recovery from the cells prepared from the nasal mucosa, the cells were subjected to freeze-and-thaw twice and $1 \times 10^5$ cells suspended with RPMI-1640 were injected into the allantoic cavity of chicken eggs. After 48-hr incubation, the allantoic fluid was harvested and subjected to hemagglutination (HA) assay to detect SeV as described (Kato, A. et al. 1996. *Genes Cells* 1:569-579).

As shown in Table 3, the virus was recovered from the swab at day 4 in all the six animals. At day 7, the virus was recovered in two of the four cynomolgus macaques, both of which showed higher gag RNA level in the nasal mucosa. At day 13, no virus was recovered in both the animals. Further, we examined if the virus could be recovered from $1 \times 10^5$ cells prepared from the nasal mucosa (Table 3). The virus was recovered from the samples at day 4 but not from those at day 7 or day 13. These results indicate that SeV/SIVgag replication level reached the peak in not more than a week.

TABLE 3

Recovery of SeV

| | | from Nasal Swab | | | from Nasal Mucosa | | |
|---|---|---|---|---|---|---|---|
| Group | Macaques | day 0 | day 4 | day 7 | day 13 | day 4 | day 7 | day 13 |
| I-A | C3880 | − | + | | | + | | |
|  | C4325 | − | + | | | + | | |

TABLE 3-continued

| | | Recovery of SeV | | | | | | |
|---|---|---|---|---|---|---|---|---|
| | | from Nasal Swab | | | | from Nasal Mucosa | | |
| Group | Macaques | day 0 | day 4 | day 7 | day 13 | day 4 | day 7 | day 13 |
| I-B | C3993 | − | + | − | | − | | |
| | C4240 | − | + | + | | − | | |
| I-C | C3882 | − | + | − | − | | | − |
| | C4324 | − | + | + | − | | | − |

5-2. SeV/SIVgag Expression in the Local LN of the Nasal Cavity in Cynomolgus Macaques Significant level of gag RNA was also found in the retropharyngeal LN and the submandibular LN, both of which receive the primary lymphocyte drainage from the nasal cavity (FIG. 5C and FIG. 5D). The gag RNA level in the LN was about 1/20 of that in the nasal mucosa in each animal at day 7 and day 13. At day 4, however, the gag RNA level in the retropharyngeal LN was not more than 1/50 of that in the nasal mucosa in each animal. Thus, no significant difference in the levels in the LN was observed between at day 4 and at day 7.

5-3. SeV/SIVgag Expression in Other Tissues in Cynomolgus Macaques

We also examined the gag expression in other tissues as shown in Table 4. We could not obtain enough cells of the palatine tonsil, but the expression level was shown to be less than that in the retropharyngeal LN. The expression in the trachea was detectable in two points; at day 4 in C3880 and at day 7 in C4240. The expression in the former was much higher than that in the latter. The expression in the lung was detected only in C3880 (at day 4). No expression was observed in the thymus or the inguinal LN. In the spleen, the expression was hardly detected; poor expression was detected only in one animal (at day 7). In PBMC, two of the four cynomolgus macaques showed gag expression at day 7, whereas no expression was observed at day 4 or day 13. In all the examined tissues shown in Table 4, the gag expressions were much less than those in the nasal mucosa, the retropharyngeal LN, and the submandibular LN.

EXAMPLE 6

Gag-Specific CD8+ T Cell Stimulation by SeV/SIVgag Infected Cells

We examined if SeV/SIVgag-infected cells can really stimulate Gag-specific CD8+ T cells in vitro by flow-cytometric analysis of antigen-specific intracellular IFN-γ induction. We used PBMC derived from a rhesus macaque chronically infected with SIV. Rhesus macaques (*Macaca mulatta*) used in this experiments were maintained in accordance with the institutional guideline for laboratory animals. These macaques were tested negative for SeV and SIV before use. Blood collection, sampling of the nasal swab, and vaccination were performed under ketamine anesthesia. This animal previously received a proviral DNA vaccination followed by challenge infection with SIVmac239 (Kestler, H. et al. 1990. *Science* 248:1109-1112) as described (Matano, T. et al. 2000. *Vaccine* 18:3310-3318). By $^{51}$Cr-release assay, SIV Gag-specific cytotoxic T lymphocyte (CTL) activity was confirmed during the chronic phase of SIV infection (data not shown).

The antigen-specific IFN-γ induction was detected by flow-cytometry as follows. The autologous herpesvirus papio-immortalized B lymphoblastoid cells (BLC) (Voss, G. et al. 1992. *J. Virol. Methods* 39:185-195) were infected with a control vaccinia virus vector (Vv-control) (Mackett, M. et al. *Proc. Natl. Acad. Sci. USA* 79:7415-7419), a recombinant vaccinia virus vector expressing SIV Gag (Vv-Gag), or a control SeV vector (SeV/control) at m.o.i. of 5, and one day later, used as control non-specific, Gag-specific, or SeV-specific stimulator as described (Gea-Banacloche, J. C. et al. 2000. *J. Immunol.* 165:1082-1092).

In culture tube (Falcon #3033), $1 \times 10^6$ PBMC were cocultured with $1 \times 10^3$ stimulator cells described above in 1 ml of RPMI-1640 with 10% FBS. After 1-hr incubation, cells were added with 0.75 µl/ml of GolgiStop (monesin) (Pharmingen, San Diego, Calif.) and incubated further for 5 hr.

In case of stimulation by p27 (Example 7), $1 \times 10^6$ PBMC were incubated in 1 ml of RPMI-1640 with 10% FBS and containing 2 µg of anti-CD28 monoclonal antibody (Becton Dickinson, San Jose, Calif.) and 10 µg of recombinant SIV

TABLE 4

Expression of gag RNA

| | Autopsy at day 4 | | | | | | PBMC | | |
|---|---|---|---|---|---|---|---|---|---|
| Group I-A | Palatine tonsil | Trachea | Lung | Thymus | Spleen | Inguinal LN | at day 4 | | |
| C3880 | 5.4 | 370 | 0.91 | <0.54 | <0.54 | <0.97 | <1.4 | | |
| C4325 | <27 | <98 | <0.54 | ND$^a$ | <0.54 | <1.1 | <1.0 | | |

| | Autopsy at day 7 | | | | | | PBMC | | |
|---|---|---|---|---|---|---|---|---|---|
| Group I-B | Palatine tonsil | Trachea | Lung | Thymus | Spleen | Inguinal LN | at day 4 | at day 7 | |
| C3993 | <12 | <3.9 | <0.54 | ND | <0.54 | <1.1 | ND | <3.6 | |
| C4240 | <12 | 7.3 | <0.54 | <1.3 | 0.98 | <2.5 | <2.5 | 3.9 | |

| | Autopsy at day 13 | | | | | | PBMC | | |
|---|---|---|---|---|---|---|---|---|---|
| Group I-C | Palatine tonsil | Trachea | Lung | Thymus | Spleen | Inguinal LN | at day 4 | at day 7 | at day 13 |
| C3882 | <5.4 | <4.0 | <2.4 | ND | <1.1 | <2.4 | <7.0 | <2.8 | <1.9 |
| C4324 | <36 | <1.8 | ND | ND | ND | <0.79 | <18 | 6.7 | <4.2 |

$^a$not determined

Gag p27 protein in culture tube. After 3-hr incubation, cells were added with 0.75 µl/ml of GolgiStop and incubated further for 15 hr.

Then, intracellular IFN-γ staining was performed by using Cytofix-Cytoperm kit (Pharmingen) according to the manufacturer's protocol. Specifically, the, stimulated cells were collected, stained at room temperature for 20 min with mixture of antibodies against surface molecules. Anti-human CD8 PerCP (Becton Dickinson) and anti-human CD3 APC (Pharmingen) antibodies were used as antibodies. Then, the cells were washed with PBS containing 0.5% bovine serum albumin (PBS-BSA), fixed and permeabilized with Cytofix-Cytoperm, and stained at 4° C. for 30 min with anti-human IFN-γ PE (Pharmingen). Stained samples were collected by FACScalibur and analyzed using CellQuest software (Becton Dickinson). For each sample, 100,000 to 200,000 total events were acquired in case of stimulation by BLC, and 50,000 to 100,000 total events were acquired in case of stimulation by recombinant protein. Gating was performed on mononuclear cells and then on CD3+CD8+ subpopulations. The ratio of CD3+CD8+IFN-γ+ cell number per mononuclear cell number was evaluated and shown as CD8+IFN-γ+ T cell number per $1\times10^6$ lymphocytes.

Figure 6:
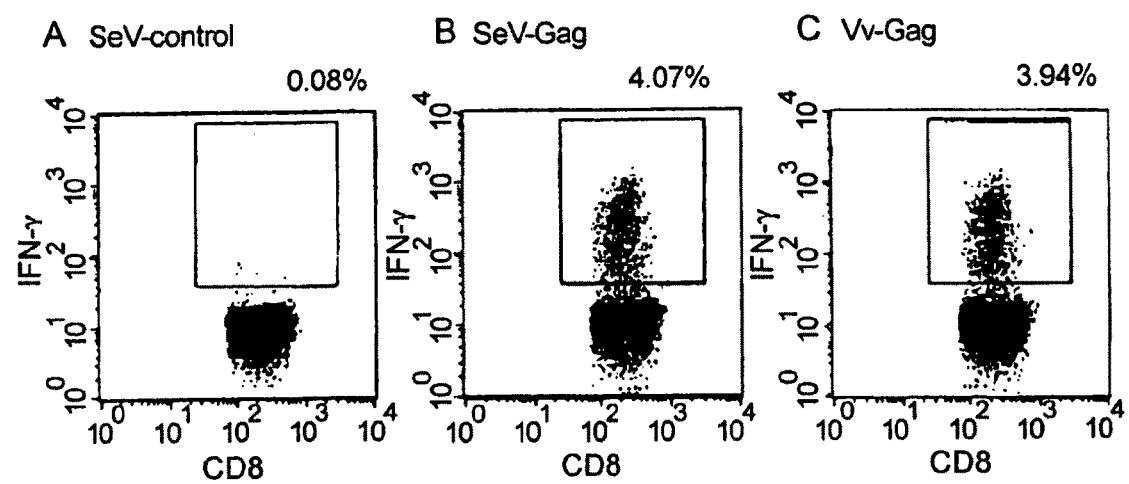
FIG. 6 shows flow-cytometric detection of intracellular IFN-γ induction after stimulation with SeV/SIVgag-infected cells. PBMC from a SIV-infected rhesus macaque were cocultured with autologous BLC infected with SeV/control (A), SeV/SIVgag (B), and Vv-Gag (C), respectively. Dot plots gated on CD3+CD8+ lymphocytes are shown. Percent of cell number surrounded by a square to the gated cell number (% IFN-γ+) in each dot plot is shown.

Coculture of the PBMC with the autologous BLC infected with a recombinant SIV Gag-expressing vaccinia virus (Vv-Gag) showed SIV Gag-specific intracellular IFN-γ induction in CD8+ T cells (FIG. 6C). Similar frequencies of CD8+IFN-γ+ T cells were observed in the PBMC coculture with SeV/SIVgag-infected BLC (FIG. 6B). No significant induction of CD8+IFN-γ+ T cells was found in the PBMC coculture with SeV/control-infected BLC (FIG. 6A). These results indicate that the SeV/SIVgag-infected BLC stimulated Gag-specific CD8+ T cells efficiently.

EXAMPLE 7

Gag-Specific CD8+ T Cell Frequencies in Rhesus Macaques

Five rhesus macaques were used for another experiment to analyze the primary immune responses after SeV-vaccination (Table 2, Group II). Two of them in group II-A (R004 and R014) received an intranasal inoculation of SeV/control, and three in group II-B (R013, R015, and R017) received that of SeV/SIVgag. R010 received a control DNA vaccination (800 µg of pCMVN DNA (Matano, T. et al. 2000. *Vaccine* 18:3310-3318) by intramuscular inoculation and 10 µg of pCMVN DNA by gene gun four times) from 12 weeks to 6 weeks before the SeV/control vaccination for another experiment. None of them showed apparent clinical symptom after the inoculation.

Figure 7:
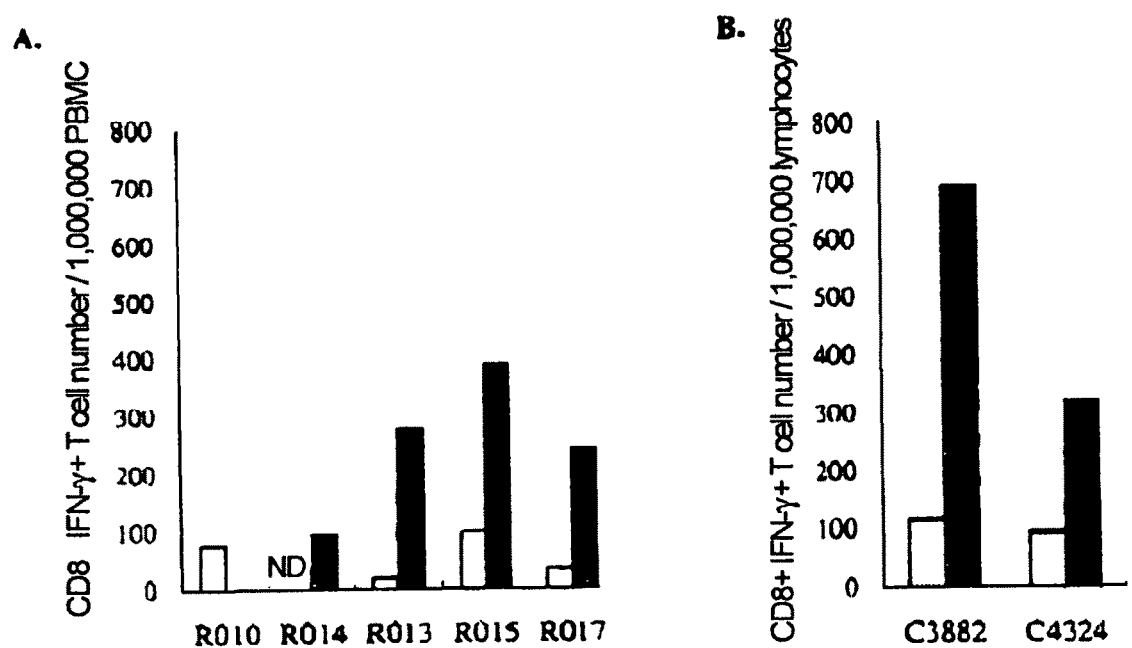
FIG. 7 shows Gag-specific CD8+IFN-γ+ T cell frequencies in the vaccinated rhesus macaques. (A) PBMC at week 3 in the group II rhesus macaques were cocultured with BLC infected with Vv-control (open box) or Vv-Gag (closed box) and subjected to flow-cytometric analysis. ND, not determined. (B) The retropharyngeal LN-derived cells at week 2 in the group I-C rhesus macaques were incubated in the absence (open box) or presence (closed box) of SIV Gag p27 and subjected to flow-cytometric analysis.

PBMC obtained at week 3 were cocultured with the autologous BLC infected with Vv-Gag and induction of IFN-γ in CD8+ T cells was examined. In all the group II-B rhesus macaques inoculated with SeV/SIVgag, significant frequencies of CD8+IFN-γ+ T cells were detected after the Gag-specific stimulation but not after the non-specific stimulation (FIG. 7A). On the contrary, no significant IFN-γ induction in CD8+ T cells was observed after the Gag-specific stimulation in the group II-A rhesus macaques inoculated with SeV/control. These results indicate the systemic immune responses, induction of Gag-specific CD8+ T cells, in SeV/SIVgag-vaccinated rhesus macaques.

Further, we examined the local immune responses around the nasal cavity by using the cells prepared from the retropharyngeal LN in the group I-C macaques. Because we failed to prepare the autologous BLC from the group I rhesus macaques, Gag-specific stimulation was performed by using a recombinant SIV Gag p27 protein. In both the group I-C rhesus macaques, significant frequencies of CD8+IFN-γ+ T cells reactive to p27 were detected, indicating induction of p27-specific CD8+ T cells in the LN.

EXAMPLE 8

SeV-Specific CD8+ T Cell Frequencies in Rhesus Macaques

Figure 8:
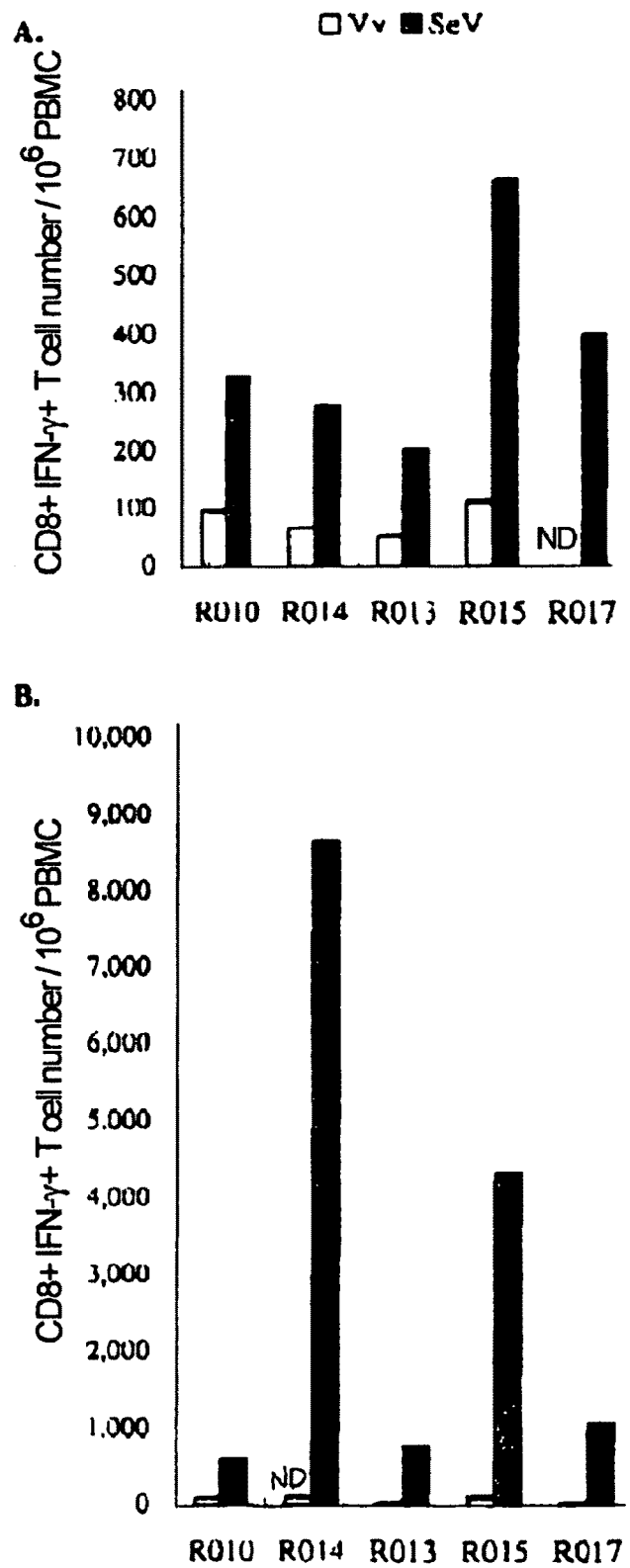
FIG. 8 shows SeV-specific CD8+IFN-γ+ T cell frequencies in the vaccinated rhesus macaques. PBMC at week 1 (A) or week 3 (B) in the group II rhesus macaques were cocultured with BLC infected with Vv-control (open box) or SeV/control (closed box) and subjected to flow-cytometric analysis. ND, not determined.

SeV-specific cellular immune responses were also examined in rhesus macaques after SeV/control- or SeV/SIVgag-inoculation. High frequencies of SeV-specific CD8+ T cells were detected at week 3 in PBMC of all the group II animals (FIG. 8B). Further analysis showed that significant frequencies of SeV-specific CD8+ T cells appeared already at week 1 in all of them (FIG. 8A). Thus, high magnitudes of SeV-specific cellular immune responses were induced quickly after the vaccination.

The protein level in plasma was evaluated by antibody ELISA. Anti-SeV antibody ELISA was performed by using inactivated SeV (Watanabe, T. et al. 2000. *Arch. Dermatol.* 136:1518-1522). Anti-SIV Gag p27 antibody ELISA was performed by using a recombinant p27 protein (ImmunoDiagnostics, Woburn, Mass.). The plasma samples were diluted by 1000-fold for the anti-SeV antibody ELISA and by 100-fold for the anti-p27 antibody ELISA.

Figure 9:
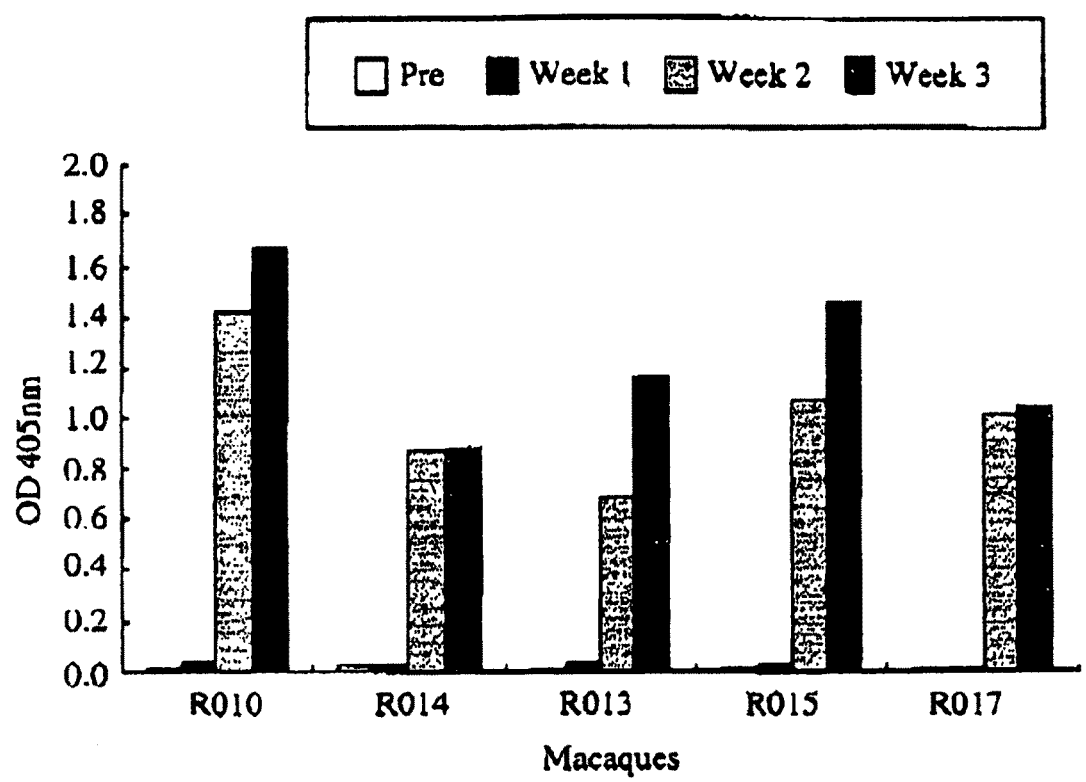
FIG. 9 shows plasma anti-SeV antibody levels detected by ELISA in the vaccinated rhesus macaques. The kinetics of the absorbance obtained with plasma diluted 1:1000 are shown. OD, optical density.

In all the group II rhesus macaques, plasma anti-SeV antibody was undetectable at week 1, but significant level of the antibody appeared at week 2 after the vaccination (FIG. 9). On the contrary, plasma anti-Gag antibody was undetectable even in the group II-B rhesus macaques inoculated with SeV/SIVgag (data not shown).

EXAMPLE 9

Prime-Boost Effect of Combination with DNA Vaccine

Figure 10:
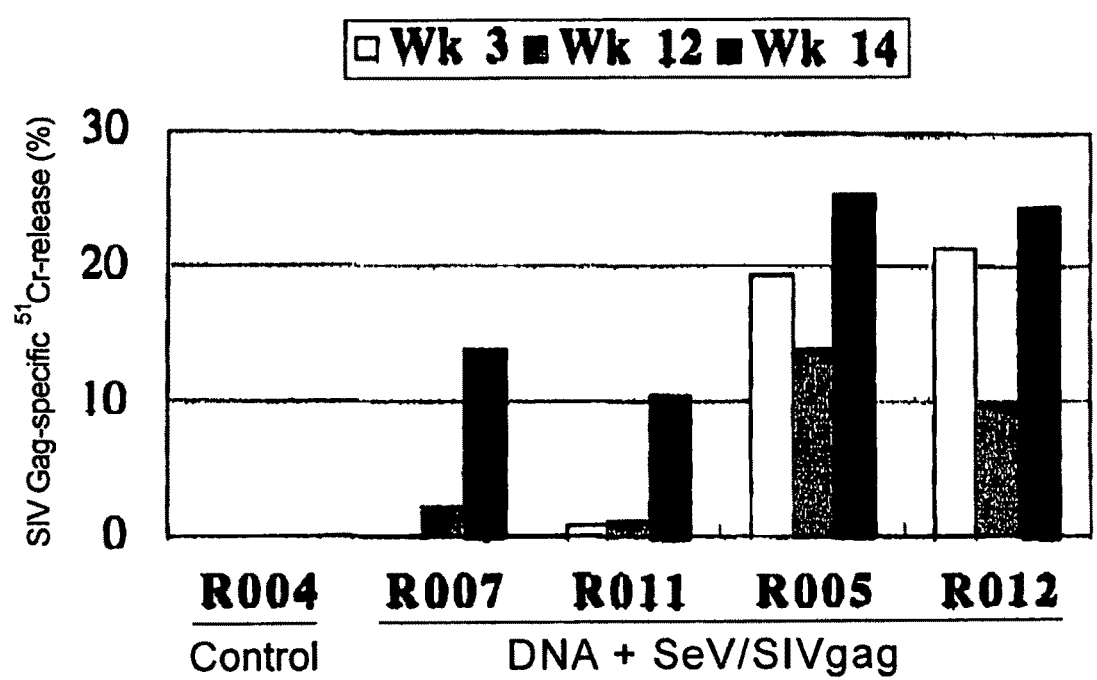
FIG. 10 shows induction of SIV Gag-specific CTL by DNA vaccine+SeV/SIVgag vaccine. SIV Gag-specific $^{51}$Cr release is shown. Effect of booster immunization by SeV/SIVgag administration (week 12) is shown. Compare week 12 with week 14.
Figure 11:
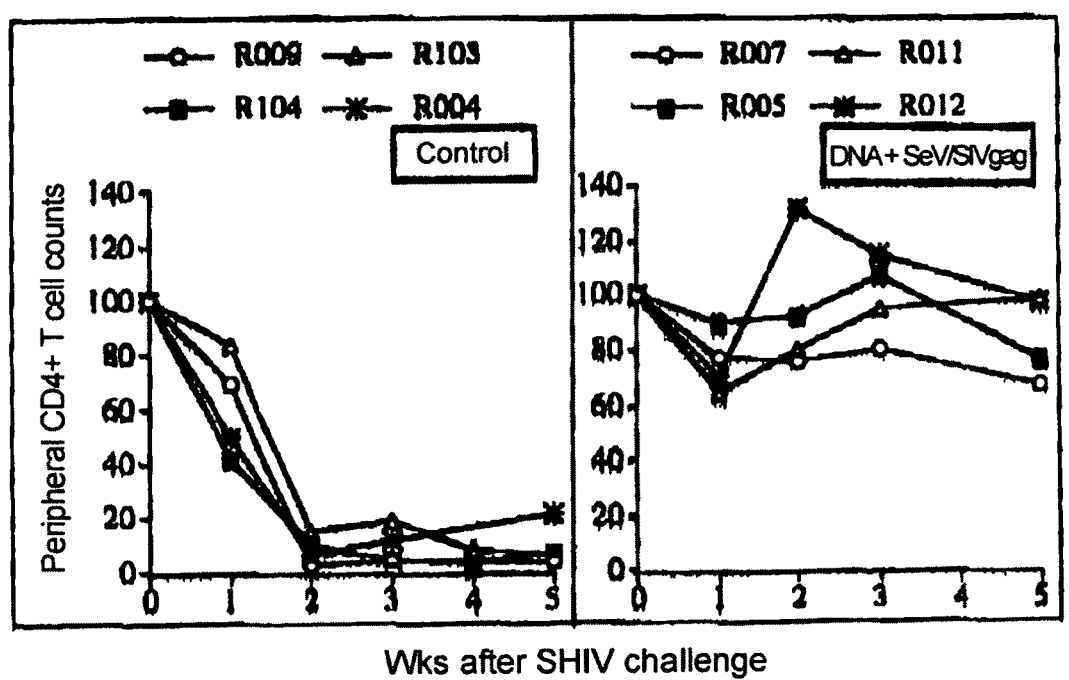
FIG. 11 shows infection protection against pathogenic SHIV challenge by DNA vaccine+SeV/SIVgag vaccine. Changes in counts of peripheral blood CD4 T cells are shown. While CD4-depletion was observed for all of four individuals in control group 2 weeks after the challenge, all of four individuals in DNA vaccine+SeV/SIVgag vaccine-administered group were protected from CD4-depletion.
Figure 12:
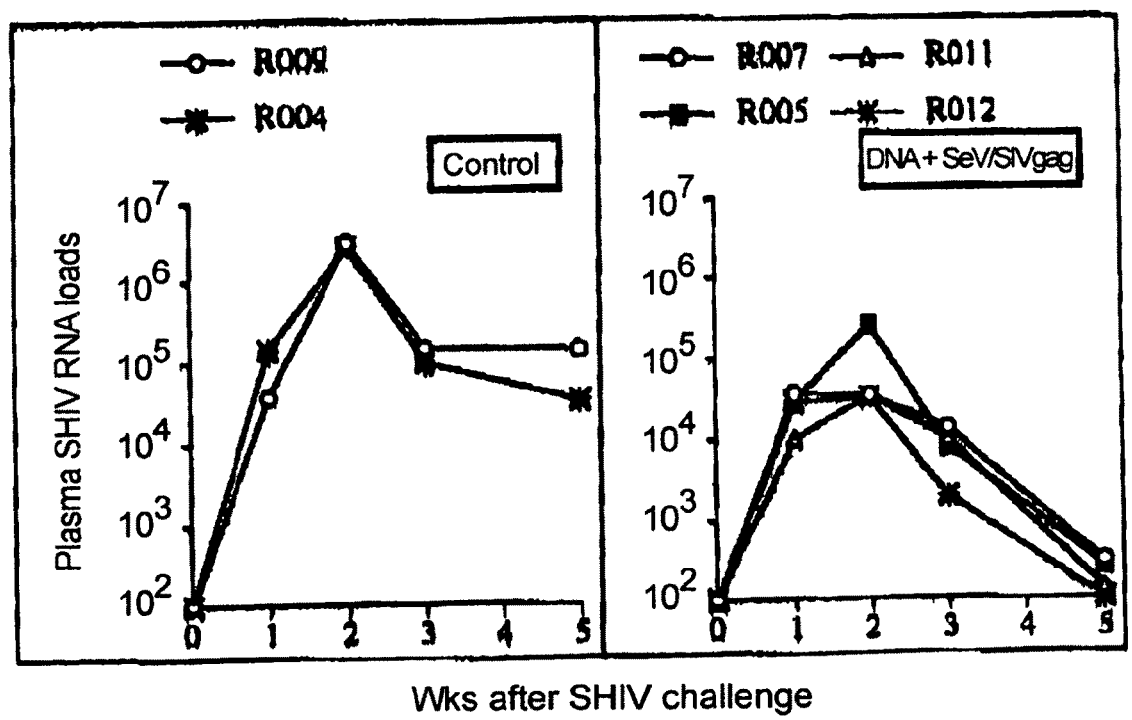
FIG. 12 shows infection protection against pathogenic SHIV challenge by DNA vaccine+SeV/SIVgag vaccine. Changes in copy numbers of SHIV RNA in plasma are shown. Copy numbers of SHIV RNA in DNA vaccine+SeV/SIVgag vaccine-administered group show significantly lower value from infection acute phase, compared with control group.

Effect of combination with DNA vaccine is tested in vaccination by prime-boost. Protocol of experiment using rhesus macaques is shown in. Table 5. DNA vaccination was performed by intramuscular (i.m.) inoculation and with gene gun (Bio-Rad) following the literature (Matano, T. et al., Vaccine 18; 3310-3318, 2000). In i.m. inoculation, 800 µl of 0.25 µg/µl DNA solution dissolved in PBS was injected to quadriceps by 200 µl at a time. Moreover, gene gun inoculation was performed by injection into the front skin of femur (Matano, T. et al., Vaccine 18: 3310-3318, 2000). There were 4 individuals in the control group, and there were 4 individuals in the DNA vaccine+SeV/SIVgag vaccine-administered group. For details of DNA vaccine, see to the literatures (Donnelly, J. J. et al., Annu. Rev. Immunol. 15: 617-648, 1997; Lu, S. et al., J. Virol. 70: 3987-3991, 1996; Matano, T. et al., Vaccine 18: 3310-3318, 2000). As mentioned above, $10^8$ CIU of SeV/SIVgag was intranasally inoculated. Twenty-six weeks after vaccination was started, 10 TCID50 of simian-human immunodeficiency virus (SHIV 89.6-PD) (Lu, Y. et al., J. Acquir. Immune Defic. Syndr. Hum. Retrovirol. 19(1): 6-18, 1998) was exposed by intravenous injection. Induction of SIV Gag-specific CTL by DNA vaccine+SeV/SIVgag vaccine was observed and changes in counts of peripheral blood CD4 showed infection protection against pathogenic SHIV challenge for all of four individuals in the administered group (FIGS. 10 and 11). Copy numbers of SHIV RNA in plasma in DNA vaccine+SeV/SIVgag vaccine-administered group show significantly lower value from infection acute phase, compared with control group (FIG. 12).

TABLE 5

| | Macaque Protocol: DNA + SeV | | | | |
|---|---|---|---|---|---|
| | Immunization | | | Challenge | |
| Animal ID | DNA-prime | | SeV-boost | (10 TCID50) | IV |
| R009 | — | | — | SHIV89.6PD | |
| R103 | — | | — | SHIV89.6PD | |
| R104 | — | | — | SHIV89.6PD | |
| R004 | Control DNA | 4 times** | SeV/control | wk 12 | SHIV89.6PD | wk 26 |
| R007 | DNA* | 4 times** | SeV/SIVgag | wk 12 | SHIV89.6PD | wk 26 |
| R011 | DNA* | 4 times** | SeV/SIVgag | wk 12 | SHIV89.6PD | wk 26 |
| R005 | DNA* | 4 times** | SeV/SIVgag | wk 12 | SHIV89.6PD | wk 26 |
| R012 | DNA* | 4 times** | SeV/SIVgag | wk 12 | SHIV89.6PD | wk 26 |

**SIV env(−)nef(−) (SIVgagpol) DNA (IM & Gene Gun)
*on wks 0, 0.5, 1, and 6

What is claimed is:

1. A vaccine comprising a recombinant Sendai virus gene-transfer vector encoding in its genome an immunodeficiency viral protein selected from the group consisting of Gag, Pol, gp41, gp160, Tat, and Gag-Pol fusion protein, wherein the vaccine induces an immune response specific to the immunodeficiency viral protein and wherein the Sendai virus vector is defective in a Sendai virus envelope gene.

2. The vaccine of claim 1, wherein the envelope gene is F gene.

3. The vaccine of claim 1, wherein the immunodeficiency viral protein is selected from the group consisting of Gag, Pol, gp41, Tat, and Gag-Pol fusion protein.

4. The vaccine of claim 1, wherein the immunodeficiency viral protein is Gag.

5. A composition comprising a carrier and a recombinant Sendai virus gene-transfer vector encoding in its genome an immunodeficiency viral protein, wherein the immunodeficiency viral protein comprises a protein selected from the group consisting of Gag, Pol, gp41, gp160, Tat, Rev, Vpu, Vpx, Vpr, Vif, Nef, Gag-Pol fusion protein, and a part of any of them, and wherein the composition induces an immune response specific to the immunodeficiency viral protein and wherein the Sendai virus vector is defective in a Sendai virus envelope gene.

6. The composition of claim 5, wherein the immunodeficiency viral protein is selected from the group consisting of Gag, Pol, gp41, Tat, and Gag-Pol fusion protein or a part of it.

7. The composition of claim 5, wherein the envelope gene is F gene.

8. The composition of claim 6, wherein the envelope gene is F gene.

9. The composition of claim 5, wherein the immunodeficiency viral protein is Gag.

10. The composition of claim 5, wherein the part comprises an epitope.

11. The composition of claim 5, wherein the immunodeficiency viral protein is in the form of a protease-processed protein.

12. The composition of claim 11, wherein the protease-processed protein is selected from the group consisting of MA(p17), CA(p24), NC(p9), p6, p10, p50, p15, p31, and p65.

13. A method for vaccination, the method comprising intranasally administering to a subject a recombinant Sendai virus gene-transfer vector encoding in its genome an immunodeficiency viral protein, thereby inducing an immune response specific to the immunodeficiency viral protein, wherein the immunodeficiency viral protein comprises a protein selected from the group consisting of Gag, Pol, gp41, gp160, Tat, and Gag-Pol fusion protein.

14. The method of claim 13, wherein the vaccination comprises multiple vaccine inoculations and the subject is inoculated with the recombinant Sendai virus vector at least once.

15. The method of claim 13, wherein the method further comprises the step of intramuscularly or intradermally inoculating the subject with a DNA vaccine comprising a naked DNA encoding the genome of the immunodeficiency virus before the inoculation with the Sendai virus vector.

16. The method of claim 13, wherein the Sendai virus vector is defective in a Sendai virus envelope gene.

17. The method of claim 16, wherein the envelope gene is F gene.

* * * * *

UNITED STATES PATENT AND TRADEMARK OFFICE
CERTIFICATE OF CORRECTION

PATENT NO. : 8,217,019 B2
APPLICATION NO. : 12/701303
DATED : July 10, 2012
INVENTOR(S) : Kano et al.

It is certified that error appears in the above-identified patent and that said Letters Patent is hereby corrected as shown below:

Cover page, under item (73), Assignees, replace

"Japan as Represented by the Director General of National Institute of Infectious Disease" with --Japan as Represented by Director General of National Institute of Infectious Diseases--.

Cover page, under item (75) Inventors, replace

"Munehide Kano, Hino (JP)" with --Munehide Kano, Tokyo (JP)--;

"Tetsuro Matano, Adachi-ku (JP)" with --Tetsuro Matano, Tokyo (JP)--;

"Atsushi Kato, Hamura (JP)" with --Atsushi Kato, Tokyo (JP)--;

"Mamoru Hasegawa, Tsukuba (JP)" with --Mamoru Hasegawa, Ibaraki (JP)--.

Page 2, Col. 2, Line 1, under OTHER PUBLICATIONS, in Matano et al., "No Significant...", replace "Proetection" with --Protection--.

Column 1, Lines 8-9, replace "now abandoned which" with --now abandoned, which--.

Signed and Sealed this
Fourth Day of December, 2012

David J. Kappos
*Director of the United States Patent and Trademark Office*

CERTIFICATE OF CORRECTION (continued)
U.S. Pat. No. 8,217,019 B2

Column 4, Lines 57-63, replace

"*In press). The gag RNA level was higher than the SeV N mRNA level probably because the former contained the genomic RNA in addition to the mRNA. Another explanation is that the gag mRNA level is expected to be higher than the latter because the gag position is upstream to the N position in the genome (Nagai, Y. 1999. Rev. Med. Virol. 9:83-99).*"

with

--In press). The *gag* RNA level was higher than the SeV N mRNA level probably because the former contained the genomic RNA in addition to the mRNA. Another explanation is that the *gag* mRNA level is expected to be higher than the latter because the *gag* position is upstream to the N position in the genome (Nagai, Y. 1999. *Rev. Med. Virol.* 9:83-99).--.

Column 9, Lines 41-42, replace "on week were" with --on week 12 were--;

Line 64, replace "an week 22" with --on week 22--.

Column 10, Line 42, replace "CD4-deplition" with --CD4-depletion--.

Column 11, Line 24, replace "tubulin. and its" with --tubulin and its--.

Column 14, Line 21, replace "amain" with --a main--;

Line 63, replace "gemone" with --genome--.

Column 25, Line 66, replace "binding.to" with --binding to--.

Column 26, Line 6, replace "(Xu Met al.," with --(Xu M et al.,--;

Line 21, replace "immnodeficiency" with --immunodeficiency--.

CERTIFICATE OF CORRECTION (continued)
U.S. Pat. No. 8,217,019 B2

Columns 29-30, in Table 1,

| Wks after the initial vaccination |
|---|
| 0  1  2    4   5    14   15 |
| 1st SeV   2nd SeV   3rd SeV   (22) | should be

| Wks after the initial vaccination |
|---|
| 0  1  2    4   5    14   15   22 |
| 1st SeV   2nd SeV   3rd SeV |

.